US006902730B1

(12) United States Patent
Kimura et al.

(10) Patent No.: US 6,902,730 B1
(45) Date of Patent: Jun. 7, 2005

(54) SEMAPHORIN GENE: SEMAPHORIN W

(75) Inventors: Toru Kimura, Kusatsu (JP); Kaoru Kikuchi, Takarazuka (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/284,180

(22) PCT Filed: Oct. 3, 1997

(86) PCT No.: PCT/JP97/03549

§ 371 (c)(1),
(2), (4) Date: Jun. 9, 1999

(87) PCT Pub. No.: WO98/15628

PCT Pub. Date: Apr. 16, 1998

(30) Foreign Application Priority Data

Oct. 9, 1996 (JP) ............................................ 8-287636

(51) Int. Cl.$^7$ ........................ A01N 63/00; C12N 15/00; C12N 15/63; C07H 21/02; C07H 21/04

(52) U.S. Cl. .................. 424/93.2; 435/320.1; 435/455; 536/23.1; 536/23.5

(58) Field of Search .............................. 536/23.1, 23.5; 424/93.2; 435/320.1, 455, 375, 69.1; 514/44

(56) References Cited

U.S. PATENT DOCUMENTS

| | | | | |
|---|---|---|---|---|
| 5,416,197 | A | 5/1995 | Raper et al. | 530/387.9 |
| 5,639,856 | A | 6/1997 | Goodman et al. | 530/328 |
| 5,684,133 | A | 11/1997 | Schwab et al. | 530/350 |
| 5,807,826 | A | 9/1998 | Goodman et al. | 514/12 |
| 5,807,862 | A | 9/1998 | Klein et al. | 517/269 |
| 5,935,865 | A | 8/1999 | Goodman et al. | 436/501 |

FOREIGN PATENT DOCUMENTS

| | | |
|---|---|---|
| EP | 0396719 B1 | 11/1990 |
| WO | WO 9417831 | 8/1994 |
| WO | WO 9507706 | 3/1995 |
| WO | WO 97/17368 A1 | 5/1997 |

OTHER PUBLICATIONS

Skolnick et.al.; From genes to protein structure and function: novel applications of computational approaches in the genomic era, 2000, TIBECH, vol. 18: 34–39.*
Kaye et al., A single amino acid substitution results in a retinoblastoma protein defective in phosphorylation and oncoprotein binding, Sep. 1990, Pro. Natl. Sci., vol. 87, pp. 6922–6926.*
Hillier et al., EST Accession No. R54387, May 1995.*
Bentley et al., a_geneseq36 Accession No. R71384, May 1995.*
Igarashi et al., N_Geneseq_0401, Accession No. Q56609, 1994.*
Hiller et al., EST Accession No. H24181, 1995.*
Kennel, D., 1971, Progr. Nucl. Acid Res. Mol. Biol., vol. 11, p. 259–301.*
Matthes et al., Cell, vol. 81, 631–639 (1995).
Messersmith et al., Neuron, vol. 14, 949–959 (1995).
Clifford J. Woolf, Nature, vol. 378, 439–440 (1995).
Eckhardt et al., Molecular and Cellular Neuroscience 9, 409–419 (1997).
Koppel, Neuron, vol. 19, 531–537 (1997).
Furuyama et al., The Journal of Biological Chemistry, vol. 271, No. 52, 33376–33381 (1996).
Mangasser–Stephan et al., Biochemical and Biphysical Research Communications 234, 153–156 (1997).
Herold et al., The Journal of Immunology, "CD100 Is Associated with CD 45 at the Surface of Human T Lymphocytes," 5262–5268 (1996).
Zhou et al., Molecular and Cellular Neuroscience 9, 26–41 (1997).
Schwab et al, Annu. Rev. Neurosci 16, 565–595 (1993).
Richardson et al., Nature, vol. 284, 264–265 (1980).
David et al., Science, vol. 214, 931–933 (1981).
Schnell et al., Nature, vol. 343, 269–272 (1990).
Luo et al., Cell, vol. 75, 217–227 (1993).
Bregman et al., Nature, vol. 378, 498–501 (1995).
Dodd et al, Cell, vol. 81, 471–474 (1995).
Kolodkin et al., Neuron, vol. 9, 831–845 (1992).
Puschel et al., Neuron, vol. 14, 941–948 (1995).
Kolodkin et al., Cell, vol. 75, 1389–1399 (1993).
Schwab et al., The Journal of Neuroscience 8(7), 2381–2393 (1988).
Bandtlow et al., Science, vol. 259, 80–83 (1993).
Luo et al., Neuron, vol. 14, 1131–1140 (1995).
Alan R. Johnson, BioEssays, vol. 15, No. 12, 807–813 (1993).
Hillier et al., Database Accession No. H10623, Jul. 2, 1995, XP–002214826.
Auffray et al., Database Accession No. Z45329, Nov. 6, 1994, XP–002214827.
Auffray et al., Database Accession No. Z42773, Nov. 6, 1994, XP–002214828.
Caroni et al., *The Journal of Cell Biology*, vol. 106, No. 4, Apr. 1, 1988, XP–000600980.
M.D. Adams et al, Nature Genetics 4(4) (1993) pp. 373–380.
Ashwani Khanna et al.; Biochemical and Biophysical Research Communications; vol. 204; No. 3; Nov. 15, 1994; pp. 1061–1066.

* cited by examiner

*Primary Examiner*—Shin-Lin Chen
(74) *Attorney, Agent, or Firm*—Birch, Stewart, Kolasch & Birch, LLP

(57) ABSTRACT

The present invention provides Semaphorin W inhibiting neurite outgrowth, and a gene therefor, as well as other Semaphorins hybridizing to said Semaphorin W gene, modified proteins or partial peptides of said Semaphorin W, antibodies against said Semaphorin W, antisense nucleotides against said Semaphorin W gene, and the use of such substances as pharmaceutical or diagnostic agents or laboratory reagents. The present invention further provides a method of screening for Semaphorin W antagonists employing said Semaphorin W, Semaphorin W antagonists obtained by said screening method, pharmaceutical agents comprising such antagonists, and transgenic animals involving said Semaphorin W.

6 Claims, 6 Drawing Sheets

SEMAPHORIN GENE: SEMAPHORIN W

This application is the national phase under 35 U.S.C. §371 of PCT International Application No. PCT/JP97/03549 which has an International filing date of Oct. 3, 1997 which designated the United States of America.

TECHNICAL FIELD

The present invention relates to Semaphorin W, a novel Semaphorin belonging to the Semaphorin family, and use of Semaphorin W for pharmaceutical or diagnostic agents or laboratory reagents. More particularly, it relates to Semaphorin W inhibiting neurite outgrowth, and a gene therefor, as well as other Semaphorins hybridizing to said Semaphorin W gene, modified proteins or partial peptides of said Semaphorin W, antibodies against said Semaphorin W, antisense nucleotides against said Semaphorin W gene, antagonists of said Semaphorin W, transgenic animals, and use of such substances as pharmaceutical or diagnostic agents or laboratory reagents.

BACKGROUND ART

It is widely known that a central nervous system (CNS)-neuron in higher organisms such as human is not capable of regeneration once injured. Therefore, one who has received an injury on his (her) spinal cord due to, for example, a traffic accident, is compelled to spend the rest of his (her) life in a hemiplegic state. On the contrary, it is known that a peripheral nervous system (PNS)-neuron retains a vigorous regeneration ability even in those higher organisms, and therefore, neurons in a limb, when disconnected, can gradually regenerate with a concomitant recovery of their function.

In the early nineteen-eighties, a group of Aguayo et al. found that when PNS-neuron is experimentally grafted into an injured CNS-neuron in a higher organism, axon growth of CNS-neuron is induced. This observation demonstrated that CNS-neuron in higher organisms which had been generally considered not to have a regeneration ability can regenerate if a suitable environment is provided (*Nature,* 284, 264–265 (1980), *Science,* 214, 931–933 (1981)). That report suggests a possibility that in CNS of higher organisms, there may exist a factor, namable "CNS-neuron regeneration inhibitor", which inhibits the regeneration of CNS-neuron, and that a release from such inhibition may allow the regeneration of CNS-neurons. This suggestion paved the way for a CNS-neuron regeneration therapy.

In 1988; a group of Schwab et al. demonstrated that there existed such CNS-neuron regeneration inhibitor among proteins derived from CNS myelin. They also succeeded in purifying, though partially, a protein having said CNS-neuron regeneration inhibition activity, and named this protein fraction NI35/250 (*Annu. Rev. Neurosci.,* 16, 565–595 (1993)), although no one has succeeded in its isolation, identification and gene cloning yet. In addition, they immunized animals with the partially purified NI35/250, and succeeded in obtaining an antibody (IN-1) having a neutralizing activity. This antibody is capable of recognizing the band for NI35/250 in Western blotting, and capable of staining, in an immunostaining, the region to which NI35/250 is supposed to be distributed. Furthermore, they demonstrated that administration of this antibody to an animal experimentally received an injury on its spinal cord has promoted regeneration of axons in spinal cord, though partially, within 2–3 weeks, and restored its function within 2–3 months (*Nature,* 343, 269–272 (1990), *Nature,* 378, 498–501 (1995)). These findings are of great value, because they experimentally demonstrated that there existed a CNS-neuron regeneration inhibitor as suggested by Aguayo et al. (supra) and that CNS-neuron can be regenerated by inhibiting the activity of said inhibitor. The above antibody is, however, directed not to human but to rat NI35/250, and exhibits a low stability and specificity. In addition, although regeneration of CNS-neuron was observed as described above by administering said antibody, its effect was so partial and incomplete that not all of the motor functions could be restored. It is, therefore, believed essential in solving these problems to identify the gene for NI35/250 or similar CNS-neuron regeneration inhibitor, and, based on knowledges of molecular biology, neuroscience and the like, develop an antagonist more effectively inhibiting the CNS-neuron regeneration inhibition activity, or develop a method for inhibiting the expression of the gene for said regeneration inhibitor.

Apart from the above, the nervous system, whether it is central or peripheral, requires formation of a complicated neural network among neurons or between neurons and peripheral receivers or effectors during development, that is, in the stage of embryo or fetus, in order to precisely carry out its principal functions, i.e., to transfer and process the information. To establish the neural network, an ingenious mechanism is necessary, which precisely guides a growing neurite to the target site locating remote therefrom.

It has been hitherto believed that a factor which positively controls the neurite outgrowth, such as neurite growth promoter and neurite growth attractant may play a major role in the formation of the neural network. However, it is now being demonstrated by recent studies on the mechanism of the network formation that the opposite factor, that is, a negative factor having an outgrowth inhibition activity is important for an accurate guidance (*Cell,* 78, 353–356 (1994)).

A representative factor having such an outgrowth inhibition activity is a protein called "Semaphorin". Semaphorin firstly discovered is Fasciclin IV found in grasshopper. Collapsin (latterly named Collapsin I) was subsequently discovered in chick (*Cell,* 75, 217–227 (1993); *Neuron,* 9, 831–845 (1992)). To date, more than 10 genes belonging to the Semaphorin family have been reported in a wide range of species covering insects such as *drosophila* and beetle, human, and viruses (*Cell,* 81, 471–474 (1996)). These Semaphorins characteristically contain in their amino acid sequences similar structures called semaphorin domains each consisting of about 600 amino acids (*Neuron,* 14, 941–948 (1995); *Cell,* 75, 1389–1399 (1993)). However, the homologies of the primary amino acid sequences in semaphorin domains among these Semaphorin genes are 80–20%, and not necessarily high.

Of these Semaphorins, functions have been verified for only a few, including, for example, Fasciclin IV of grasshopper, Semaphorins I and II of *drosophila*, Collapsin of chick, and Semaphorin III which corresponds to Collapsin in mammals. All of these Semaphorins are known to inhibit neurite outgrowth or synapsis formation. In particular, Semaphorin III has been reported to have an activity collapsing in a short time the growth cone of cultured neuron (growth-cone collapse activity) in vitro (*Neuron,* 14, 941–948 (1996); *Neuron,* 14, 949–959 (1995); *Cell,* 81, 631–639 (1995); *Cell,* 75% 1389–1399 (1993); *Cell,* 75, 217–227 (1993); *Neuron,* 9, 831–845 (1992)).

Although it is now being demonstrated, as described above, that known Semaphorins have a growth-cone collapse activity and a neurite outgrowth inhibition activity during development, and play a role in giving an accurate guidance to neuron, it is not evident at present whether or not the Semaphorins exert some function not only during development but also in the adult, and less evident whether or not Semaphorins play a role as a CNS-neuron regeneration inhibitor. Of course, since known Semaphorins have been shown to be a negative to guidance factor inhibiting neurite outgrowth, it would not be unreasonable to consider said Semaphorins as a candidate for a CNS-neuron regeneration inhibitor (*Nature,* 378, 439–440 (1995)). However, it has been shown by in vitro experiments that Semaphorin III (Sema III), only one Semaphorin of higher organisms of which function has been analyzed, exerts its neurite-outgrowth inhibition activity on a sensory neuron and sympathetic neuron both of which are peripheral, but not on a retinal neuron which is central (*Cell,* 75, 217–227 (1993)). In addition, Northern analysis on the distribution of Sema III expression in the adult carried out by the present inventors has revealed that it is expressed mainly in peripheral tissues (see Reference example 2 below). It is therefore hardly believed that Sema III having such features has a function as a CNS-neuron regeneration inhibitor.

Problem to be Solved by the Invention

The present invention aims to provide Semaphorin W, a novel Semaphorin belonging to the Semaphorin family, and a gene therefor, and to provide pharmaceutical agents for neural diseases, in particular for regeneration of CNS-neuron, and related diagnostic agents or laboratory reagents. More specifically, the present invention aims to provide Semaphorin W which inhibits neurite outgrowth and a gene therefor, as well as other Semaphorins hybridizing to said Semaphorin W gene, modified proteins or partial peptides of said Semaphorin W, antibodies against said Semaphorin W, antisense nucleotides against said Semaphorin W gene, and use of such substances as pharmaceutical or diagnostic agents or laboratory reagents. The present invention further aims to provide a method of screening for Semaphorin W antagonists employing said Semaphorin W, Semaphorin W antagonists obtained by said screening method, pharmaceutical agents comprising such antagonists, and transgenic animals regarding said Semaphorin W.

Means of Solving the Problem

In order to provide pharmaceutical agents for neural diseases, in particular for regeneration of CNS-neuron, and related diagnostic agents or laboratory reagents, the present inventors have planed to identify a novel Semaphorin which has not yet been cloned. In particular, the present inventors have paid their attention to the similarity between the in vitro activities of the above-described NI35/250 and the negative guidance factor Semaphorin, i.e., to the fact that NI35/250 has a growth-cone collapse activity and a neurite-growth inhibition activity in vitro (*J. Neurosci.,* 8, 2381–2393 (1988); *Science,* 259, 80 (1993)), while known Semaphorins similarly possess a neurite-growth inhibition activity, and particularly Semaphorin III has also a growth-cone collapse activity. This suggested to the inventors the possibility that unknown Semaphorins which have not yet been identified may include the one inhibiting regeneration of CNS-neuron. Specifically, the present inventors' idea was that Semaphorin having those characteristics that 1) it is highly expressed in the CNS of the adult, but 2) it is poorly expressed in other tissues where regeneration of neuron (or neurite outgrowth) is not inhibited, such as peripheral tissues in the adult and fetus tissues, has not been identified yet, and if one can identify a new unknown Semaphorin having such characteristics, the Semaphorin might be involved in inhibition of regeneration of CNS-neuron.

First of all, the inventors have searched EST (Expressed Sequence Tags) database for DNA sequences encoding the amino acids relatively well conserved among previously reported Semaphorin genes. As a consequence, the DNA fragment T09073 (SEQ ID NO:15) was identified, which encodes, as a partial sequence, a sequence: Gln-Asp-Pro-Val0Cys-Ala-Trp (SEQ ID NO:12), similar to that consisting of seven amino acids extremely well conserved among Semaphorins (Gln(or Arg)-Asp-Pro-Tyr-Cys-Ala(or Gly)-Trp) (SEQ ID NO:13).

The T09073 gave a sequence information as to only 364 bp and contained undetermined bases, and further, the open reading frame could not be determined. It was, therefore, utterly impossible at that stage to conclude that T09073 corresponds to part of a gene encoding "Semaphorin". Furthermore, although T09073 has been submitted to the database as a sequence derived from a human child brain cDNA library, it was unknown whether or not the sequence is expressed in the fetus or peripheral tissues of the adult, and therefore, it could not be concluded that the sequence corresponds to part of a novel Semaphorin gene specifically expressed in the CNS.

Thus, the present inventors firstly carried out Northern analysis using a DNA fragment consisting of 196 base pairs from the 5' region of T09073 as a probe, in order to check the distribution of expression of a gene containing T09073. As a result, it was found that the gene corresponding to T09073 was highly and widely expressed in CNS tissues in the adult, whereas among the other tissues, it was expressed only in the lung and spleen of the adult throughout the fetal and postnatal periods. It was thus demonstrated that the gene exhibited a distribution pattern of expression expected for a novel Semaphorin gene at which the present inventors aimed.

Next, the present inventors cloned the gene containing T09073 in full length in order to ascertain whether it is a novel Semaphorin or not. Specifically, a rat cDNA library was screened using the above DNA fragment consisting of 196 base pairs as a probe. As a result, the gene thus cloned proved to be a novel Semaphorin gene having a sequence characteristic to Semaphorins. We named this novel Semaphorin "Semaphorin W".

Further analysis revealed that Semaphorin W has an effect as a novel Semaphorin gene at which the present inventors aimed, that is, an inhibition activity against neurite outgrowth, especially an inhibition activity for CNS-neurons.

Semaphorin W of the present invention appears to be involved in inhibition of regeneration of CNS-neuron in the adult, since it is highly expressed in CNS in the adult and has an inhibitory effect on CNS-neurons as described above. Semaphorin W may be used to screen for Semaphorin W antagonists, and those antagonists identified in such screening system are expected to promote regeneration of CNS-neuron. Similarly, antisense DNAs or RNAs against Semaphorin W gene are also expected to promote regeneration of CNS-neuron as well as the above antagonists.

In addition, in view of the fact that Semaphorin W of the present invention has also an inhibitory effect on PNS-neurons, it may be used as a therapeutic or diagnostic agent for pains or immune diseases such as atopic dermatitis, by administering it to peripheral tissues, which results in the inhibition of neurite outgrowth of PNS-neuron. Furthermore, Semaphorin W is a novel Semaphorin belonging to the Semaphorin family which has unprecedented features regarding its distribution of expression and its effect as described above. Semaphorin W, therefore, serves as an important research material or a laboratory reagent.

The present invention has been completed on the basis of the above findings.

Thus, the gist of the present invention relates to:

(1) a gene encoding the following protein (a) or (b):

(a) Semaphorin W protein comprising the amino acid sequence shown in SEQ ID NO: 3, (b) a protein which comprises an amino acid sequence wherein one or more amino acids are deleted, substituted and/or added in the amino acid sequence shown in SEQ ID NO: 3, and which protein inhibits neurite outgrowth;

(2) a gene comprising the following DNA (c), (d), or (e):

(c) Semaphorin W DNA comprising the base sequence shown in SEQ ID NO: 1 or 2, (d) DNA which hybridizes under stringent conditions to DNA comprising the base sequence shown in SEQ ID NO: 1 or 2, and which encodes a protein inhibiting neurite outgrowth, (e) DNA of the above item (d) which contains the base sequence shown in SEQ ID NO: 4 or 5 and/or the base sequence shown in SEQ ID NO: 10;

(3) a gene comprising DNA which hybridizes under stringent conditions to DNA comprising the base sequence shown in SEQ ID NO: 7, and which encodes a protein having a semaphorin domain;

(4) a protein obtained by expressing a gene of any one of the above items (1) to (3);

(5) a gene encoding a protein comprising an amino acid sequence wherein one or more amino acids are deleted, substituted and/or added in the amino acid sequence shown in SEQ ID NO: 3, and which protein promotes neurite outgrowth;

(6) a protein obtained by expressing a gene of the above item (5);

(7) DNA which is cloned from a human cDNA library or a human genomic library, and which hybridizes under stringent conditions to DNA comprising at least part of DNA consisting of the base sequence shown in SEQ ID NO: 1, 4, or 10;

(8) an expression plasmid which expresses either a gene of any one of the above items (1) to (3) and (6), or DNA of the above item (7);

(9) a transformant transformed with an expression plasmid of the above item (8);

(10) a process for producing a recombinant protein, which process comprises culturing a transformant of the above item (9), and recovering the recombinant protein expressed;

(11) a peptide comprising a segment of at least six or more amino acids of a protein of the above item (4) or (6);

(12) a peptide of the above item (11) which promotes neurite outgrowth;

(13) a peptide of the above item (11) characterized in that it contains the glutamic acid residue at position 204 of the amino acid sequence shown in SEQ ID NO: 3 or an amino acid residue corresponding to the position of said glutamic acid residue;

(14) an antisense nucleotide, or chemically modified variant thereof, which is directed against a segment of at least eight or more bases of a gene of any one of the above items (1) to (3), or of DNA of the above item (7);

(15) an antisense nucleotide, or chemically modified variant thereof, of the above item (14), characterized in that it inhibits expression of a protein of the above item (4);

(16) an antibody against a protein of the above item (4) or (6), or against a peptide of any one of the above items (11) to (13);

(17) a pharmaceutical agent comprising, as an active ingredient, a gene of any one of the above items (1) to (3) and (5), DNA of the above item (7), a protein of the above item (4) or (6), a peptide of any one of the above items (11) to (13), an antisense nucleotide or chemically modified variant thereof of the above item (14) or (16), or an antibody of the above item (16);

(18) a method of screening for Semaphorin W antagonists, characterized in that it employs a protein of the above item (4);

(19) Semaphorin W antagonist obtained by the screening method of the above item (18);

(20) Semaphorin W antagonist of the above item (19) which comprises a protein of the above item (6), a peptide of any one of the above items (11) to (13), or an antibody of the above item (16);

(21) a CNS-neuron regeneration promoter, characterized in that it contains at least one of the antisense nucleotides or chemically modified variants thereof of the above item (14) or (15), or Semaphorin W antagonists of the above item (19) or (20);

(22) a neurite outgrowth inhibitor for PNS-neuron, characterized in that it contains at least one of the proteins of the above item (4); and

(23) a transgenic animal in which either a gene of any one of the above items (1) to (3) and (5), or DNA of the above item (7) has been artificially inserted into its chromosome, or has been knocked out.

MODE FOR CARRYING OUT THE INVENTION

The 1st embodiment of the present invention is (a) a gene encoding Semaphorin W protein which comprises the amino acid sequence shown in SEQ ID NO: 3, or (b) a gene encoding a protein which comprises an amino acid sequence wherein one or more amino acids are deleted, substituted and/or added in the above amino acid sequence shown in SEQ ID NO: 3 and which protein inhibits neurite outgrowth. The 2nd embodiment of the present invention is (c) a gene comprising Semaphorin W DNA which comprises the base sequence shown in SEQ ID NO: 1 or 2, or (d) a gene comprising DNA which hybridizes under stringent conditions to the above DNA comprising the base sequence shown in SEQ ID NO: 1 or 2 and which encodes a protein inhibiting neurite outgrowth, or (e) a gene comprising DNA of the above item (d) which comprises the base sequence shown in SEQ ID NO: 4 or 5 and/or the base sequence shown in SEQ ID NO: 10. These genes are explained below in order.

1) Gene Encoding Semaphorin W (Semaphorin W Gene)

Of the above-mentioned genes, "a gene encoding Semaphorin W protein which comprises the amino acid sequence shown in SEQ ID NO: 3" or "a gene comprising Semaphorin W DNA which comprises the base sequence shown in SEQ ID NO: 1 or 2" is a gene encoding rat Semaphorin W. Among these genes, the DNA comprising the base sequence shown in SEQ ID NO: 2 corresponds to the open reading frame of the rat Semaphorin W gene shown in SEQ ID NO: 1. These genes may be cloned, as described in Example 3, by screening a cDNA library derived from rat CNS tissues or a genomic library using a probe (for example, a DNA probe having the base sequence shown in SEQ ID NO: 7) prepared on the basis of the sequence of "T09073" found in EST database. Particular techniques for such cloning may be found in the standard texts such as "Molecular Cloning", 2nd ed., Cold Spring Harbor Laboratory Press (1989). The base sequence of the cloned DNA may also be determined by conventional methods, for example, using a sequencing kit commercially available.

Alternatively, after publication of the base sequence of rat Semaphorin W cDNA of the present invention, one skilled in the art can also easily clone the gene encoding rat Semaphorin W by using part of said cDNA as a probe or PCR primer, without using cloning methods described above.

2) Gene Encoding Modified Protein of Semaphorin W

Of the above-mentioned genes, "a gene encoding a protein which comprises an amino acid sequence wherein one or more amino acids are deleted, substituted and/or added in the amino acid sequence shown in SEQ ID NO: 3 and which protein inhibits neurite outgrowth" refers to a gene encoding a so-called "modified proteins" of Semaphorin W which inhibits neurite outgrowth. Those skilled in the art may easily obtain a gene encoding such protein, for example, by site-directed mutagenesis (Methods in Enzymology, 100, 448– (1983)) or PCR method ("Molecular Cloning", 2nd ed., Chapter 15, Cold Spring Harbor Laboratory Press (1989); "PCR A Practical Approach", IRL Press, 200–210 (1991)). In this context, the number of amino acid residues to be deleted, substituted and/or added is to be such a number that permits the deletion, substitution and/or addition by well-known methods such as site-directed mutagenesis described above.

For the purpose of the present invention, the phrase "inhibiting neurite outgrowth" means that the protein has the collapse activity for growth cone of neuron, or that the protein has the neurite-outgrowth inhibition activity. These activities may be measured with a test substance such as an expression product of DNA encoding Semaphorin W or modified protein thereof, for example, in the following manner.

Since Semaphorin W is a membrane protein, it exists in the cell membrane of the cells transformed with Semaphorin W gene. The activities of the above test substance may, therefore, easily be measured by using the membrane fraction of the transformed cells as a test material.

Examples of activity measurement include measurement of collapse activity for growth cone of neuron (M. Igarashi et al., *Science*, vol. 259, pp. 77–79 (1993)), or measurement of neurite-outgrowth inhibition activity (e.g., J. A. Davies et al., *Neuron*, vol. 2, pp. 11–20 (1990) and M. Bastmeyer, *J. Neurosci.,* vol. 11, pp. 626–640 (1991)). A method of measuring the growth-cone collapse activity is described in detail in literature (M. Igarashi et al., *Science*, vol. 269, pp. 77–79 (1998)). Briefly, the measurement may be carried out by a method in which cells expressing a test substance such as Semaphorin W is homogenized, and the homogenate containing the cell membrane fraction or the purified membrane fraction is used (E. C. Cox et al., *Neuron*, vol. 2, pp. 31–37 (1990)), or by a method in which a protein extracted from the membrane fraction is used as such (*Neuron*, vol. 2, pp. 21–29 (1990)) or is used as a test material after reconstituting it in a liposome (C. E. Bandtlow, *Science*, vol. 259, pp. 80–84 (1993)), or by a method in which a solubilized protein modified not to bind the cell membrane is used (*Neuron* vol. 18, pp. 383–396 (1997)). In order to measure the growth-cone collapse activity in practice using these materials, a test substance such as Semaphorin W in one of the forms as describe above is added to neurons cultured under conventional conditions (e.g., "Culturing, Nerve Cells" edited by Banker et al., MIT Press (1991)) in a chamber coated with a substance promoting the neurite outgrowth and the growth-cone formation such as laminin, collagen, polylysine or polyornithine. After the addition, when a sufficient time has passed to induce collapse of growth cone (typically from 30 minutes to one hour after the addition), those neurons are fixed with 1% glutaraldehyde or the like, and the number of the growth cones which have been collapsed is counted under a microscope. In this measurement, it is important that another sample is used as a control, which is prepared from cells not expressing the test substance such as Semaphorin W according to the completely same procedures as those used for the test substance-expressing cells. Typically, normalization of the samples is conducted on the basis of the total amounts of protein included within the samples. To measure the neurite-outgrowth inhibition activity, part of the surface of a micropore filter or a culture container made of glass or plastics is coated with a test substance such as Semaphorin W prepared as described above, and the activity is indicated, for example, by the inability of neurons cultured under conventional conditions to adhere to the coated area, or by a remarkable decrease in the rate of neurite outgrowth on the coated area, or by the inability of invasion of growing neurites from the outside of the coated area into the coated area because of its stopping on the border between the coated and non-coated areas or its avoidance from the coated area. Furthermore, a stripe assay (Development 101, 685–696 (1987)), a modification of the above method in which the surface is coated in stripes alternately using two kinds of test substances, may also be used to measure the neurite outgrowth inhibition activity. When a cluster of cells expressing a test substance is co-cultured with neurons in a collagen gel, the inability of outgrowing neurite to enter the cluster of cells expressing the test substance may also be used as an indicator (A. Sophia et al., *Cell*, vol. 81, 621–629 (1995)).

Both of CNS and PNS neurons may be used as the cells for the above activity measurements. As described in the section "BACKGROUND ART", CNS in adult mammals naturally contains a large amount of regeneration (outgrowth) inhibitor. It is, therefore, @ 15 extremely difficult to measure in vivo an inhibitory effect on neurite outgrowth of CNS-neuron, and such inhibitory effect is usually measured by an in vitro method as described above. Since these in vitro methods each have individual characteristics, it is preferred to use more than one method to confirm the activity. Although preferred neurons used for a measurement of the activity are CNS-neurons such as motor neurons in spinal cord or motor cortex, or retinal ganglion cells, PNS-neurons of superior cervical ganglion and dorsal root ganglion may also be used because NI35/250 known as a CNS-neuron regeneration inhibitor has proved to have effects such as neurite-growth inhibition and growth-cone collapse activities also on such PNS-neurons (*J. Cell Biol.,* 106, 1281–1288 (1988); *Science,* 2 μg, 80–83 (1993)).

Examples of the modified proteins of this embodiment may include modified proteins of human or rat Semaphorin W, and more particularly, include the modified proteins as described below.

Based on the structural comparison of known Semaphorins, most of the conserved amino acids are located in the semaphorin domain, suggesting that these conserved amino acids are essential for expression of the Semaphorin activity. Furthermore, the present inventors have found that a modified Sema III protein in which aspartic acid residue at position 198 in its semaphorin domain has been substituted with glycine did not have the growth-cone collapse activity (see Reference example 1 below). Accordingly, the aspartic acid residue at position 198 of Sema III is believed essential for expression of the activity. When the amino acid residues corresponding to this position were compared among known Semaphorins, it was shown that they are extremely well conserved and are all aspartic acid residue with a few exceptions in which glutamic acid residue is located at this position. It is, therefore, believed that the amino acid residue at this position is also essential for expression of the activity of Semaphorins other than Sema III. In Semaphorin W of the present invention, the amino acid residue corresponding to the position 198 of Sema III is presumed to be glutamic acid residue at position 204 of the amino acid sequence shown in SEQ ID NO: 3, while in the after-mentioned amino acid sequence of human Semaphorin W shown in SEQ ID NO: 6, it is presumed to be glutamic acid residue at position 16.

Considering the above information, it is desirable to make the above-described deletions, substitutions and/or additions of amino acids at positions other than those conserved among Semaphorins, in order to retain the activity of Semaphorin W in modified proteins. Particularly, it is desirable not to modify the glutamic acid residue at position 204 in rat Semaphorin W shown in SEQ ID NO: 3 and the glutamic acid residue at position 16 in human Semaphorin W shown in SEQ ID NO: 6. On the other hand, in order to displace the amino acid residues conserved among Semaphorins while retaining the activity of Semaphorin W, it is desirable to substitute an amino acid residue having a similar side chain for the amino acid residue to be substituted. By substituting such amino acid having a similar side chain for a conserved amino acid, it may be possible to produce a modified protein which has an enhanced activity of Semaphorin W. Such modified protein having the enhanced activity is highly suitable as a neurite-outgrowth inhibitor for PNS-neuron as will be described hereinafter in the section of the 22nd embodiment of the present invention.

In the above-noted embodiment, “a conserved amino acid” refers to an amino acid located at a position at which more than 50% of Semaphorin genes shown in FIG. 2 of *Cell,* 75, 1389–1399 (1993) or FIG. 1 of *Neuron,* 14, 941–948 (1996) encode the same amino acid.

3) DNA Hybridizing Under Stringent Conditions To Semaphorin W Gene

Of the above-mentioned DNAs, “a gene comprising DNA which hybridizes under stringent conditions to DNA comprising the base sequence shown in SEQ ID NO: 1 or 2 and which encodes a protein inhibiting neurite outgrowth” refers to a gene which hybridizes under stringent conditions to rat Semaphorin W gene comprising the base sequence shown in SEQ ID NO: 1 or 2, including all the Semaphorin W genes derived from mammals such as human and mouse.

As used herein, “a gene which hybridizes under stringent conditions” refers to such a gene that hybridizes to the above rat Semaphorin W gene, for example, when subjected to hybridization at a formamide concentration of about 45% (v/v) and a salt concentration of about 5×SSPE and at a temperature around 42° C., and washed at a salt concentration of about 2×SSPE and at a temperature around 42° C. Cloning of such genes may be achieved, for example, by screening cDNA or genomic libraries prepared from various animal tissues using all or part of DNA shown in SEQ ID. NO: 1 as a probe. An example of cDNA library used herein may be a cDNA library prepared from mRNAs derived from human CNS tissues. Such screening may be carried out consulting to the standard texts such as “Molecular Cloning” (2nd ed., Cold Spring Harbor Laboratory Press (1989)).

Specific examples of the gene of this embodiment may include all the Semaphorin W genes of mammal and avian. Between mammals or between mammal and avian, homologous genes have quite similar sequences, and usually more than 80%, in many cases more than 90%, of the base sequence are common to each other. All the mammal and avian Semaphorin W genes, therefore, correspond to this embodiment. In other words, those genes which have a homology of 80% or above are included in this embodiment, and those having a homology of 90% or above are preferred.

One specific example of a gene of this embodiment is human Semaphorin W gene containing the base sequence shown in SEQ ID NO: 4 or 5 and/or the base sequence shown in SEQ ID NO: 10. The base sequences shown in SEQ ID NOs: 4 and 6 represent DNAs encoding 687 amino acids (SEQ ID NO: 6) of the C-terminal region of human Semaphorin W, and the base sequence shown in SEQ ID NO: 5 corresponds to the open reading frame of the base sequence shown in SEQ ID NO: 4. The base sequence shown in SEQ ID NO: 10 represents DNA encoding 111 amino acids (SEQ ID NO: 11) of the N-terminal region of human Semaphorin W. Cloning of these human Semaphorin W DNA may be achieved by the screening method described above, or may also be achieved by, for example, synthesizing primers on the basis of the base sequence of rat Semaphorin W shown in SEQ ID NO: 1 and carrying out PCR reaction using cDNAs prepared from mRNAs derived from a human CNS tissue as template (see “PCR” (1991) edited by McPherson et. al., IRL Press). Similarly, the same may be cloned by using an EST clone (Genome Systems, USA).

As described above, “the base sequence shown in SEQ ID NO: 4 or 6” and “the base sequence shown in SEQ ID NO: 10” are partial base sequences of human Semaphorin W. However, one skilled in the art can easily clone the human Semaphorin W gene in full length by screening a human cDNA or human genomic library with DNA comprising part or all of said base sequence as a probe, or by using PCR method, and determine its base sequence in the same method as described above. Accordingly, such full-length human Semaphorin W gene may be one specific example of the gene of this embodiment.

The 3rd embodiment of the present invention is a gene comprising DNA which hybridizes under stringent conditions to DNA comprising the base sequence shown in SEQ ID NO: 7, and which encodes a protein having a semaphorin domain.

In the above description, “DNA comprising the base sequence shown in SEQ ID NO: 7” is DNA of which complete base sequence was determined on the basis of the sequence information as to the DNA “T09073” encoding, as a partial sequence, a sequence (Gln-Asp-Pro-Val-Cys-Ala-Trp) (SEQ ID NO:12) similar to the sequence consisting of seven amino acids well conserved among Semaphorins (Gln (or Arg)-Asp-Pro-Tyr-Cys-Ala (or Gly)-Trp) (SEQ ID NO: 13) and is a DNA fragment corresponding to the region from position 1561 to position 1756 in the base sequence of rat Semaphorin W shown in SEQ ID NO: 1, or the region from position 922 to position 1117 in the base sequence of human Semaphorin W shown in SEQ ID NO: 4.

The “stringent conditions” as used herein refers to those conditions described above in the section of the 2nd embodiment of the present invention.

Cloning of DNAs of this embodiment is achieved by, for example, hybridization with DNA of SEQ ID NO: 7, and specifically may be carried out, for example, according to the procedures described in TINS, 15, 319–323 (1992) and references cited therein, and more specifically according to the following procedures.

That is, the cloning may be achieved by screening cDNA or genomic libraries prepared from various animal tissues using DNA comprising the base sequence shown in SEQ ID NO: 7 as a probe. The screening may be carried out according to, for example, the procedures as those described in Example 3. Preferred cDNA libraries are those derived from an adult tissue of CNS, and cDNA libraries derived from hippocampus, corpus striatum, and cerebellum are more preferred. As described above, the conditions shown in Example 3 or those described in *TINS,* 15, 319–323 (1992) and references cited therein may be used for the hybridization.

The gene of this embodiment is also "DNA which encodes a protein having a semaphorin domain". As used herein, "semaphorin domain" refers to a domain consisting of 300–600 amino acid residues more than 20% of which are identical to those amino acids constituting the semaphorin domain of any one of ten known Semaphorins (G-Sema I, T-Sema, I, D-Sema II, H-Sema III, C-Collapsin, Sem A, Sem B, Sem C, Sem D, Sem E) described in, for example, *Cell,* 75, 1389–1399 (1993) or *Neuron,* 14, 941–948 (1995). Those proteins having a semaphorin domain more than 30% of which amino acids are identical to those amino acids in any one of the known Semaphorins are particularly preferred. The identity of amino acids is determined by comparison using, for example, DNASIS Ver. 2.0 (HITACHI Software Engineering) under conditions of ktup=1 and cutoff=1. More preferred proteins are those in which ten or more cysteines, particularly twelve or more cysteines, of the thirteen cysteines conserved in semaphorin domains of the ten known Semaphorins (for example, those cysteines marked in FIG. 1 on page 942 of *Neuron,* 14, 941–948 (1995)) are conserved.

Examples of such gene of this embodiment may include Semaphorin genes which hybridize under stringent conditions to DNA comprising the base sequence shown in SEQ ID NO: 7 and which contain semaphorin domains and exhibit the neurite-outgrowth inhibition activity, or all of the Semaphorin W genes of mammal and avian like the 2nd embodiment described above.

The 4th embodiment of the present invention is a protein obtained by expressing a gene of any one of the let to 3rd embodiments described above.

Typical examples of protein included in this embodiment are rat Semaphorin W having the amino acid sequence shown in SEQ ID NO: 3, and human Semaphorin W having the amino acid sequence shown in SEQ ID NO: 6 or 11. Semaphorin W has a signal sequence at its N-terminus, and said signal sequence undergoes processing to be removed during its transfer to membrane, resulting in mature Semaphorin W. The mature form of rat Semaphorin W is presumed to consist of the amino acid sequence beginning at amino acid 40 of the amino acid sequence shown in SEQ ID NO: 3, and the mature form of human Semaphorin W is presumed to consist of the amino acid sequence beginning at amino-acid 28 of the amino acid sequence shown in SEQ ID NO: 11. Since such mature form of Semaphorin W or modified protein thereof may also be obtained by expressing a gene of any one of the 1st to 3rd embodiments described above, it is also included in this embodiment.

Preparation of the proteins of this embodiment may be achieved, for example, by ligating a cloned rat Semaphorin W cDNA into a known expression vector such as pET or pCDM8, and introducing it into appropriate host cells to express and produce Semaphorin W. The host cells may be prokaryotic or eukaryotic. For example, *Escherichia coli* strains or animal cell lines are already conventionally used for such purpose and are commercially or publicly available. Examples of animal host cells include COS-1, COS-7, CHO cells and the like.

To transform appropriate animal host cells with an expression plasmid, a known procedure such as DEAE-dextran method (*Current Protocols in Molecular Biology*, F. M. Ausubel et al. ed., John Wiley & Sons (1987)) may be used. As confirmed in Examples 6 and 7, Semaphorin W exists in the cell membrane faction which contains a sufficient amount of Semaphorin W to be directly used in various assays. Therefore, various assays for activities of a protein of this embodiment may easily be carried out using a cell membrane fraction prepared from appropriate cells.

Furthermore, a protein of this embodiment may be purified by, for example, affinity purification using Semaphorin W-recognizing antibodies described hereinafter in the section of the 16th embodiment of the present invention, or conventional column chromatography.

The 5th embodiment of the present invention is a gene encoding a protein which comprises an amino acid sequence wherein one or more amino acids are deleted, substituted and/or added in the amino acid sequence shown in SEQ ID NO: 3 and which protein promotes neurite outgrowth. The 6th embodiment of the present invention is a protein obtained by expressing a gene of the 6th embodiment of the present invention.

In the genes of the 5th embodiment described above, deletions, substitutions and/or additions may be introduced in the procedures similar to those used for a gene encoding a modified protein of the 1st embodiment of the present invention. Similarly, the promotion effect on neurite outgrowth may easily be measured, for example, by adding Semaphorin W in an assay system for Semaphorin W activity described above in the section of the 1st embodiment of the present invention and further adding thereto a test substance (i.e., a candidate modified Semaphorin W protein). For details, see the descriptions in the section of the 18th embodiment of the present invention.

Specific examples of the proteins of the 6th embodiment of the present invention may be modified rat or human Semaphorin W proteins of which neurite-outgrowth inhibition activity has been eliminated. Such modified protein lacking the activities of Semaphorin W is expected to exert the promotion effect on neurite-outgrowth, when it binds to receptors for Semaphorin W in place of Semaphorin W, or to Semaphorin W itself, by inhibiting the binding of Semaphorin W to the receptors. As described above in the section of the 1st embodiment of the present invention, it has been suggested that the active site of Semaphorin may be located in the semaphorin domain, and particularly, it may probably be located at glutamic acid residue at position 204 in rat Semaphorin W shown in SEQ ID NO: 3, or glutamic acid residue at position 16 in human Semaphorin W shown in SEQ ID NO: G. Accordingly, in order to eliminate the Semaphorin W activity from the modified protein, it is desirable to introduce the deletions, substitutions and/or additions to the conserved amino acids in said semaphorin domain, preferably to the glutamic acid residue at position 204 of the amino acid sequence shown in SEQ ID NO: 3, or to the glutamic acid residue at position 16 of the amino acid sequence shown in SEQ ID NO: 6. In such cases, those substitutions in which an amino acid having a side chain of a distinct nature is substituted for the original amino acid are desirable. Also in the cases of Semaphorin W other than that from human or rat, modifications are preferably made on the amino acid residue at the position corresponding to this position 204, that is, on the amino acid residue at the position which corresponds to position 204 in the amino acid sequence shown in SEQ ID NO: 3, or to position 16 of Semaphorin W shown in SEQ ID NO: 6 when the amino acid sequence of said Semaphorin W is aligned with that of rat or human Semaphorin W so as to give the maximum identity.

Since the proteins of the 6th embodiment of the present invention promote neurite outgrowth as described above, some of these proteins will serve as CNS-neuron regeneration promoters as described hereinafter in the section of the 21st embodiment.

The 7th embodiment of the present invention is DNA which is cloned from a human cDNA library or a human genomic library, and which hybridizes under stringent conditions to DNA comprising at least part of rat or human Semaphorin W DNA shown in SEQ ID NO: 1, 4, or 10.

Methods of cloning are described in detail in, for example, "Molecular Cloning", 2nd ed., Cold Spring Harbor Laboratory Press (1989), and specifically include, for example, methods employing hybridization or PCR. Although a preferred library used herein is a genomic library derived from human, a cDNA library derived from CNS-neuron in adult human may also be used. Those methods employing hybridization may be carried out according to, for example, *TINS,* 15, 319–323 (1992) and references cited therein. Those methods employing PCR may be carried out according to, for example, "PCR" edited by McPherson et al., IRL Press (1991).

The DNAs thus cloned include not only the full length DNA but also its DNA fragments comprising more than 200 bases, or single-stranded forms (coding strands or complementary stands thereof) of said DNA fragments. Examples of DNA of the 7th embodiment of the present invention may include chromosomal DNAs containing 5' and/or 3' transcriptional control regions, noncoding sequences of exons, introns or the like, in addition to regions encoding amino acids. Such sequences which do not encode any amino acids are also quite useful, for example, in developing a medicine using antisense techniques described hereinafter.

The 8th embodiment of the present invention is an expression plasmid which expresses either a gene of the 1st, 2nd, 3rd or 5th embodiment, or DNA of the 7th embodiment of the present invention. The 9th embodiment of the present invention is a transformant transformed with an expression plasmid of the 8th embodiment. Furthermore, the 10th embodiment of the present invention is a process for producing a recombinant protein which process comprises culturing a transformant of the 9th embodiment and recovering the recombinant protein expressed. As described above in the section of the 4th embodiment of the present invention, methods of preparing an expression plasmid and a transformant, and methods of producing a recombinant protein, per se, are all well known to those skilled in the art.

The 11th embodiment of the present invention is a peptide comprising a segment of at least 6 amino acids in a protein of the 4th or 6th embodiment of the present invention. In this context, the limitation "at least 6 amino acids" is based on the fact that a minimal size of peptide capable of forming a stable structure consists of 6 amino acids, and preferred peptides are those consisting of 8 or more amino acids, more preferably of about 10–20 amino acids. A short peptide such as those consisting of about 10–20 amino acids can be synthesized on a peptide synthesizer, while a longer peptide can be obtained by preparing DNA through conventional genetic engineering, and expressing it in, for example, animal cells as described above. The peptide thus prepared can also be modified by conventional methods.

These peptides can be applied to pharmaceutical agents described hereinafter in the section of the 12th and 13th embodiments, and can also be used for producing antibodies.

The 12th embodiment of the present invention is a peptide of the 11th embodiment of the present invention which promotes neurite outgrowth. Such peptide may be prepared by the methods described above in the section of the 11th embodiment of the present invention. The promotion effect on neurite outgrowth can also be easily measured as described above in the section of the 5th embodiment of the present invention by adding Semaphorin W to an activity assay system described above in the section of the 1st embodiment of the present invention and further adding thereto a test substance (i.e., a candidate peptide of Semaphorin W). For details, see the descriptions in the section of the 18th embodiment of the present invention.

Examples of these peptides may be peptides which have lost the neurite-outgrowth inhibition activity of Semaphorin W. A peptide lacking Semaphorin W activity is expected to exert its neurite-outgrowth promotion effect, when it binds to receptors for Semaphorin W or to Semaphorin W itself, by inhibiting the binding of Semaphorin W to the receptors. Some of such peptides will serve as CNS-neuron regeneration promoters as described hereinafter in the section of the 21st embodiment.

The 13th embodiment of the present invention is a peptide of the 11th embodiment of the present invention, characterized in that it contains the glutamic acid residue at position 204 of the amino acid sequence shown in SEQ ID NO: 3 or an amino acid residue corresponding to the position of said glutamic acid residue. Such peptides may be prepared by the methods described above in the section of the 11th embodiment.

As described above in the section of the 1st embodiment of the present invention, the glutamic acid residue at position 204 of rat Semaphorin W shown in SEQ ID NO: 3 (in the case of human Semaphorin W shown in SEQ ID NO: 6, the glutamic acid residue at position 16) seems essential for expression of the Semaphorin W activity. Since this amino acid residue may possibly be involved in the binding between Semaphorin W and its receptors, a peptide of this embodiment containing said amino acid residue or an amino acid residue at the position corresponding to that of said amino acid residue may interfere the neurite-outgrowth inhibition activity of Semaphorin W by binding to receptors for Semaphorin W or to Semaphorin W itself and thereby inhibiting the binding of Semaphorin W to the receptors, resulting in promotion of neurite outgrowth. Some of the peptides having such effect will serve as CNS-neuron regeneration promoters as described hereinafter in the section of the 21st embodiment. Such neurite-outgrowth promotion activity can easily be measured as described above in the section of the 5th embodiment of the present invention by adding Semaphorin W to an activity assay system described in the section of the 1st embodiment of the present invention, and further adding thereto a test substance (i.e., a candidate peptide of Semaphorin W). For details, see the descriptions in the section of the 18th embodiment of the present invention.

In this embodiment, "an amino acid corresponding to the position of said glutamic acid residue" refers to an amino acid residue which is located at the position corresponding to position 204 in rat Semaphorin W, when the amino acid sequence of the protein of the 4th or 6th embodiment of the present invention is aligned with the amino acid sequence of rat Semaphorin W shown in SEQ ID NO: 3 so as to give the maximum identity. Accordingly, "a peptide characterized in that it contains an amino acid residue corresponding to the position of said glutamic acid residue" refers to a peptide which comprises such amino acid residue at the position corresponding to position 204 in rat Semaphorin W as well as flanking amino acids on either side thereof.

The 14th embodiment of the present invention is an antisense nucleotide, or chemically modified variant thereof, which is directed against a segment of at least eight or more bases in a gene of any one of the 1st to 3rd embodiments, or in DNA of the 7th embodiment of the present invention.

As used herein, "antisense nucleotide" refers to a so-called antisense oligonucleotide, antisense RNA, or antisense DNA, and it may be artificially prepared using a synthesizer, or may be obtained by, for example, expressing a gene in the direction opposite to the usual case (i.e., in the antisense direction). For details, see the descriptions in the section of the 21st embodiment of the present invention.

These antisense nucleotides are used for inhibiting the expression of Semaphorin W as described hereinafter in the section of the 15th embodiment of the present invention, and are also useful as laboratory reagents for, for instance, in situ hybridization. In the present invention, "a chemically modified variant" specifically refers to such a variant that is chemically modified so as to enhance the transferability of the antisense nucleotide into cells or the stability of the antisense nucleotide in the cells. Examples of such chemically modified variant are phosphorothioate, phosphorodithioate, alkyl phosphotriester, alkyl phosphonate, alkyl phosphoamidate and the like derivatives ("Antisense RNA and DNA", WILEY-LISS, 1992, pp. 1–50, *J. Med. Chem.*, 36, 1923–1937 (1993)). The chemically modified variant may be prepared according to, for example, the reference cited just above.

The 15th embodiment of the present invention is an antisense nucleotide, or chemically modified variant thereof, of the 14th embodiment described above, characterized in that it inhibits the expression of a protein of the 4th embodiment of the present invention.

mRNAs produced by usual gene transcription are sense-strands, and the antisense nucleotides or chemically modified variants thereof can bind to such sense-strand mRNAs in cells to inhibit the expression of those particular genes. Therefore, the above antisense nucleotides or chemically modified variants thereof can inhibit the expression of Semaphorin W, and can thereby inhibit the activity of Semaphorin W. Some of antisense nucleotides or chemically modified variants thereof having such effect will serve as CNS-neuron regeneration promoters as described hereinafter in the section of the 21st embodiment of the present invention.

It can easily be determined whether a particular antisense nucleotide prepared, or a chemically modified variant thereof, has a desired inhibitory effect or not, by directly introducing the antisense oligonucleotide itself or by introducing a gene which produces said antisense RNA when transcribed, into cells expressing Semaphorin W, and then determining whether the amount of the expressed Semaphorin W is decreased or not.

Examples of antisense nucleotide having such inhibitory effect are those oligonucleotides having sequences complementary to either the coding region or the 5' noncoding region of Semaphorin gene of the above-described embodiments, and those antisense nucleotides having sequences complementary to the transcription initiation site, translation initiation site, 5' noncoding region, exon-intron junction region, or 5'CAP region are desirable.

The 16th embodiment of the present invention is an antibody against a protein of the 4th or 6th embodiment, or against a peptide of any one of the 11th to 13th embodiments. Such antibody can easily be produced by using mouse or rabbit according to the procedures described in, for example, "Current Protocols in Immunology", pp. 2.4.1–2.6.6 (1992, J. E. Coligan ed.). Monoclonal antibodies can also be easily produced by the methods described in the above-mentioned reference. Such antibodies may be used in affinity chromatography or screening of cDNA libraries, and as pharmaceutical or diagnostic agents, or laboratory reagents. Some of such antibodies have the activity of neutralizing Semaphorin W. Such neutralizing activity can easily be determined, as described above in the section of the 5th embodiment of the present invention, by adding Semaphorin W to an activity assay system described in the section of the 1st embodiment of the present invention, and further adding thereto a test substance (i.e., a candidate antibody against Semaphorin W). Some of such neutralizing antibodies will serve as CNS-neuron regeneration promoters as described hereinafter in the section of the 21st embodiment of the present invention.

The 17th embodiment of the present invention is a pharmaceutical agent comprising, as an active ingredient, any one of all of the genes (DNAs), proteins, peptides, antisense nucleotides or chemically modified variants thereof, and antibodies of the present invention.

Among such pharmaceutical agents, CNS-neuron regeneration promoters and neurite-outgrowth inhibitors for PNS-neuron will be described in the sections of the 21st and 22nd embodiments of the present invention, respectively. See, therefore, the sections of the 21st and 22nd embodiments for such applications.

It is being demonstrated in recent years that certain Semaphorins play important roles not only in the nervous system but also in non-nervous systems. For example, it has been suggested that Semaphorin may probably act in inhibiting the growth of cardiac muscles (Nature, 383, 525–528 (1996)). Also in the immune system, a certain Semaphorin has been suggested to be involved in aggregation and survival of B lymphocytes (*Proc. Natl. Acad. Sci. USA,* 93, 11780–11785 (1996)). It has also been suggested more recently that a certain Semaphorin may play some role in the immune reactions in rheumatism (*B.B.R.C.,* 234, 153–156 (1997)). Furthermore, involvement of Semaphorins in lung cancer has also been suggested (*Proc. Natl. Acad. Sci. USA,* 93, 4120–4125 (1996)).

Accordingly, Semaphorin W of the present invention or its modified proteins, peptides, antisense nucleotides and the like are expected to be useful as antiallergic agents, immunosuppressive agents, or anti-tumor agents. For specific directions for use, dosage and the like of such pharmaceutical agents, see the sections of the 21st and 22nd embodiments.

The 18th embodiment of the present invention is a method of screening for Semaphorin W antagonists, characterized in that it employs a protein of the 4th embodiment of the present invention. As used herein, "Semaphorin W antagonist" refers to a substance which inhibits, for example, the neurite-outgrowth inhibition activity of Semaphorin W.

The screening is conducted by adding Semaphorin W to an assay system for Semaphorin W activity described in the section of the 1st embodiment of the present invention, and further adding thereto a test substance. In particular, inhibition of the Semaphorin W activity resulted from the addition of the test substance to the culture medium throughout the incubation period or only temporarily in the incubation period can be used as an indicator in the Semaphorin W activity assay carried out with added Semaphorin W. It is also important to confirm that the test substance alone does not influence the survival, neurite outgrowth and the like of neurons at the same concentration. When both of these requirements are fulfilled, one can consider the test substance as a Semaphorin W antagonist. Although it is preferred to prepare in advance the test substance in the form of aqueous solution, an organic solvent such as DMSO may also be used as a solvent. In any cases, it is important to minimize the volume of solvent so as to exclude any effects of the solvent on neurons. Specifically, the volume to be added should be less than an equal volume, preferably less than 1/10 volume, and more preferably less than 1/100 volume relative to the culture medium. Some of Semaphorin W antagonists thus obtained will serve as CNS-neuron regeneration promoters as described hereinafter in the section of the 21st embodiment of the present invention.

The 19th embodiment of the present invention is Semaphorin W antagonist obtained by the screening method of the 18th embodiment of the present invention. Such antagonist may have any structure and any form, provided that it inhibits the activity of Semaphorin W.

The 20th embodiment of the present invention is Semaphorin W antagonist of the 19th embodiment which comprises a protein of the 6th embodiment, a peptide of any one of the 11th to 13th embodiments, or an antibody of the 16th embodiment of the present invention. In other words, it is a protein of the 6th embodiment, a polypeptide of any one of the 11th to 13th embodiments, or an antibody of the 16th embodiment of the present invention which has an effect of inhibiting the activity of Semaphorin W. Such antagonists can be identified by subjecting one of the above substances to the screening system of the 18th embodiment of the present invention, and some of the antagonists thus identified will serve as CNS-neuron regeneration promoters as described below in the section of the 21st embodiment of the present invention.

The 21st embodiment of the present invention is a CNS-neuron regeneration promoter, characterized in that it contains at least one of the antisense nucleotides or chemically modified variants thereof of the 14th or 15th embodiment, or Semaphorin W antagonists of the 19th or 20th embodiment of the present invention. Since this embodiment relates to use of such substances in “regeneration therapy for CNS-neuron”, specific directions for use, dose and the like are described below.

1) Antisense nucleotide or chemically modified variant thereof.

Application of antisense nucleotides has been attempted in various diseases, and in recent years, it is also considered to be applicable in neurological disorders (*TINS* 20, No. 8, 321–322 (1997)).

As described above in the section of the 14th or 15th embodiment of the present invention, the antisense nucleotide or chemically modified variant thereof of the 14th or 15th embodiment of the present invention can be used for inhibiting expression of Semaphorin W gene. Accordingly, such antisense nucleotide may decrease the abundance of the Semaphorin protein, and promote regeneration of CNS-neurons. Therapeutic methods using the nucleotide or the variant include those in which the antisense oligonucleotide or its chemically modified variant is administered as such, and those in which antisense RNA is produced in cells.

In the method in which the antisense oligonucleotide or its chemically modified variant is administered as such, a preferred antisense oligonucleotide has a length of, for example, about 5–200 bases, more preferably 8–25 bases, and especially preferably 12–25 bases. Antisense oligonucleotide or its chemically modified variant may be formulated by mixing it with stabilizing agent, buffer, solvent and the like prior to its administration. Such formulation may be co-administered with, for example, an antibiotic, anti-inflammatory, or anesthetic agent. Although the formulation thus prepared may be administered via various routes, it is preferred to topically administered at a site in which neurons are notably disordered. Usually, regeneration of neuron takes several days to several months, and the formulation is administered every day or every several days to several weeks during the period. To avoid such frequent administrations, a sustained-release mini-pellet formulation may be prepared and embedded near the affected site. Alternatively, a formulation may be gradually and continuously administered to the affected site by means of, for example, an osmotic pump. The dose is typically adjusted so that the concentration at the site of action will be 0.1 nM to 10 $\mu$M.

In the method in which antisense RNA is produced in cells, a preferred antisense RNA has a length of, for example, more than 100 bases, preferably more than 300 bases, and more preferably 600 bases or more.

The methods by which a gene expressing an antisense RNA is introduced into a patient include an in vivo method in which the gene is directly introduced into cells in a living body, and an ex vivo method in which the gene is introduced into particular cells ex vivo and the cells are returned into the body (*Nikkei Science*, April, 1994, pp. 20–46; *Gekkan-Yakuji,* 36, (1), 23–48 (1994); *Jikkenn-Igaku-Zokan,* 12 (15), 1994; and references cited therein). An in vivo method is more preferred.

Such in vivo methods include a method employing recombinant viruses and other methods (*Nikkei Science*, April, 1994, pp. 20–45; *Gekkan-Yakuji,* 36 (1), 23–48 (1994); *Jikkenn-Igaku-Zokan,* 12 (15), in its entirety (1994); and references cited therein).

The methods employing recombinant viruses may include the methods in which a gene producing an antisense RNA is incorporated into a virus genome of, for example, retrovirus, adenovirus, adeno-associated virus, herpesvirus, vaccinia virus, poliovirus, or sindbis virus, and the recombinant virus is introduced into a living body. Among these methods, those employing retrovirus, adenovirus or adeno-associated virus are particularly preferred.

Other methods may include a liposome method or a lipofectin method. The liposome method is particularly preferred.

For the ex vivo methods, a micro-injection method, the calcium phosphate method, electroporation and the like may also be used, besides those techniques described above.

Administration of the gene to a patient is carried out via appropriate routes depending on, for example, the particular disease or symptom to be treated. For example, it may be administered intravenously, intraarterially, subcutaneously, or intramuscularly, or directly administered into an affected site such as neuron. For example, when spinal cord is infected with the recombinant viruses, the expression of Semaphorin gene is inhibited exclusively in the spinal cord. Expression of antisense oligonucleotide of the present invention typically lasts several days to several months, and such single infection is sufficient to allow regeneration of neuron. The gene may also be re-infected, when weakly expressed. When administered by an in vivo method, the gene may be formulated in the form of, for example, a solution, and typically it is formulated in the form of an injection containing an antisense nucleotide as an active ingredient to which conventional carrier and the like may be added, if necessary. In the case of liposomes or membrane-fused liposomes (such as Sendai virus (HVJ)-liposomes) containing an antisense nucleotide, the liposome preparations may be in the form of a suspension, a frozen preparation, a centrifugally-concentrated frozen preparation or the like.

Although the amount of antisense nucleotide in the formulation may vary depending on, for example, the disease to be treated, the age and weight of the patient, it is typically 0.0001–100 mg, and preferably 0.001–10 mg. Such formulation is administered once or more, and when administered more than twice, it is desirable to administer it every day or repeatedly at appropriate intervals.

2) Modified Protein of Semaphorin W

As described above in the sections of the 5th and 6th embodiments of the present invention, one can prepare a modified Semaphorin W of which neurite-outgrowth inhibition activity on CNS-neuron has been eliminated. When administered into a living body, such modified protein is expected to bind to receptors for Semaphorin W in place of Semaphorin W, resulting in inhibition of Semaphorin W activity and promotion of regeneration of CNS-neuron.

Such modified protein of Semaphorin W is formulated with stabilizer, buffer, and/or diluent, and administered to a patient for therapy. Such formulation may be administered via various routes, and it is preferred to topically administer to the focal site. Since regeneration of neuron typically takes several days to several months, the formulation is administered once or more in order to continuously inhibit Semaphorin W activity throughout the period. When administered more than once, it is desirable to administer it every day or repeatedly at appropriate intervals. When administered to CNS by injection, for example, into the spinal cord, several hundreds μg to 2 g, preferably less than several tens mg, are used per administration. To reduce the administration frequency, it may be administered using a sustained-release formulation or gradually administered over a long period by means of, for example, an osmotic pump. Alternatively, it may be administered by grafting cells expressing such modified Semaphorin W protein into a living body.

3) Peptide of Semaphorin W

Some of the peptides of any one of the embodiments from 11th to 13th embodiments of the present invention suppress the neurite outgrowth inhibition activity of Semaphorin W on CNS-neuron by inhibiting the binding of Semaphorin W to its receptors, resulting in promotion of CNS-neuron regeneration. Examples of peptide having such effect include a peptide characterized in that it contains glutamic acid residue at position 204 of rat Semaphorin W shown in SEQ ID NO: 3 or an amino acid residue at the position corresponding to that of said glutamic acid residue, as described above in the section of the 13th embodiment of the present invention. The suppression may be any one of competitive, noncompetitive, uncompetitive, and allosteric inhibitions.

As for the methods of formulating or administering such polypeptides, and their doses, see the above section “2) Modified protein of Semaphorin W”.

4) Antibody against Semaphorin W

A neutralizing antibody which neutralizes the activity of Semaphorin W is expected to promote the regeneration therapy of CNS-neuron by inhibiting Semaphorin W activity, when administered into a living body.

The methods of formulating or administering such neutralizing antibodies and their doses may be the same as described in the above section “2) Modified protein of Semaphorin W”. Alternatively, a method in which cells producing such monoclonal antibody are grafted directly into CNS may also be used, as described in *Nature,* 343, 269–272 (1990).

The 22nd embodiment of the present invention is a neurite outgrowth inhibitor for PNS-neuron, characterized in that it contains at least one of the proteins of the 4th embodiment of the present invention. Although the proteins of the 4th embodiment of the present invention may inhibit the neurite outgrowth of CNS-neuron, they are also expected to inhibit the neurite outgrowth of PNS-neuron, since PNS-neuron also probably expresses receptors for Semaphorin W, and receptors for other Semaphorins also probably react with Semaphorin W. Accordingly, they may serve as therapeutic agents for atopic dermatitis, pain or other diseases by virtue of their inhibition activity on neurite outgrowth of PNS-neuron.

As for the methods of formulating or administering such proteins, and their doses, see the above section “2) Modified protein of Semaphorin W”.

The 23rd embodiment of the present invention is a transgenic animal in which either a gene of any one of the 1st to 3rd and 5th embodiments, or DNA of the 7th embodiment of the present invention has been artificially inserted into its chromosome, or has been knocked out.

In the light of the gene information on Semaphorin W of the present invention, one skilled in the art can quite easily produce a transgenic animal which expresses the gene of the 1st, 4th, 7th, or 9th embodiment of the present invention, as: apparent from the following references: “Manipulation of Mouse Embryo” edited by B. Hogan et al., 1986, Cold Spring Harbor Laboratory; Shinichi Aizawa, “Gene Targeting”, 1995, Yodosha, etc. Accordingly, the transgenic animal thus produced is naturally included within the scope of the present invention. The transgenic animal thus produced is very useful as an animal model for developing pharmaceuticals or as an animal used for screening of pharmaceuticals. Furthermore, a so-called knockout animal in which the gene of the 1st, 4th, 7th, or 9th embodiment of the present invention has been deleted is characterized in that it does not contain such gene. As described in literatures, or as apparent from the common knowledge in the art, such knockout animals cannot be produced without the gene information on Semaphorin W of the present invention. It goes without saying, therefore, that such knockout animals are included within the scope of the present invention.

While Semaphorin W has an important in vivo function relating to regeneration of neurons as described above, it has been also suggested as mentioned above that Semaphorin W may have other unknown functions such as immunosuppression (*Cell,* 75, 1389–1399 (1993)). Accordingly, it is quite important to investigate the expression of Semaphorin W gene or the distribution and function of Semaphorin W protein for studying this technical field or for diagnosing patients with neurological disorders or other diseases. The present invention can also provide gene probes, antibodies, recombinant proteins, transgenic animals and the like which can be used for such purposes.

Total RNAs were extracted from various tissues of six-weeks old rats, electrophoresed on 1% agarose-formamide gel, blotted onto a filter, and hybridized with a $^{32}$P-labeled rat Semaphorin W DNA probe to determine the distribution of Semaphorin W mRNA expression. Fifteen μg of RNA was loaded in each lane. The upper panel shows the result of autoradiography. The positions corresponding to 18S and 28S ribosomal RNAs are indicated at the left margin of the panel. The lower panel shows the ethidium bromide staining of the gel. The upper and lower bands correspond 28S and 18S ribosomal RNAs, respectively.

Figure 2:
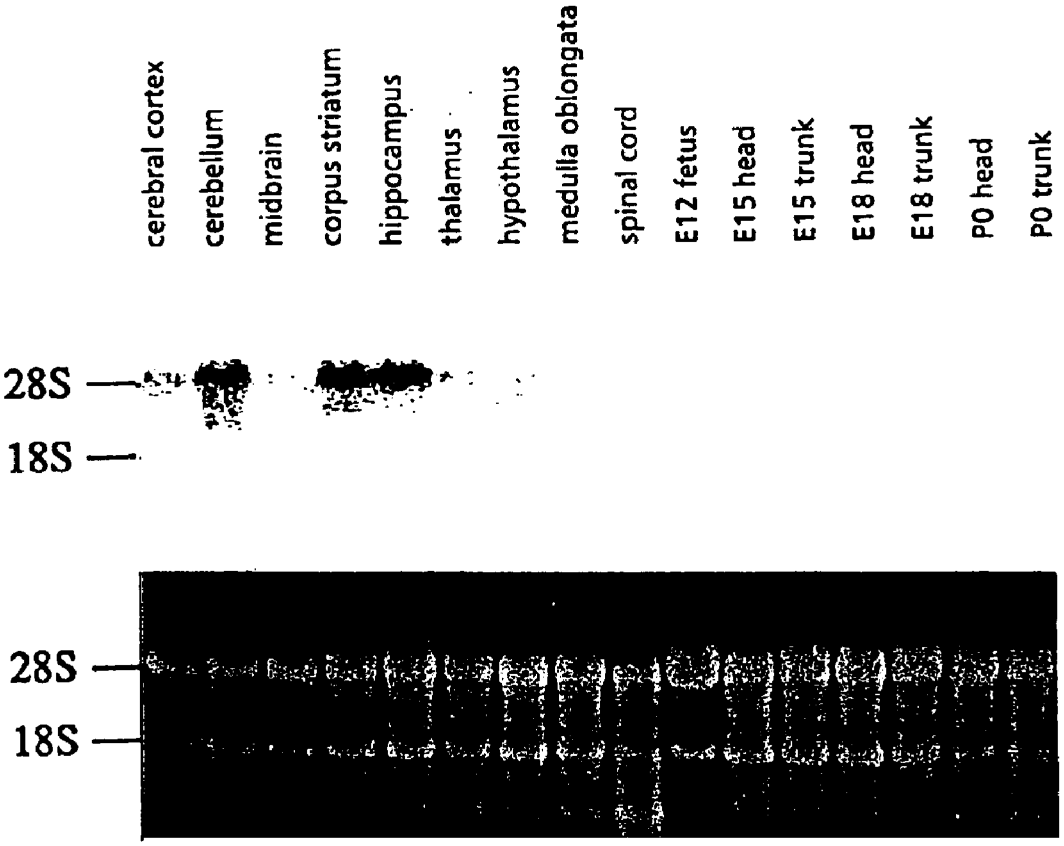

FIG. 2 shows a picture of electrophoresis indicating distribution of Semaphorin W expression in fetus and CNS tissues of the adult determined by Northern analysis.

Total RNAs were extracted from rat tissues at various ages, electrophoresed on 1% agarose-formamide gel, blotted onto a filter, and hybridized with a $^{32}$P-labeled rat Semaphorin W DNA probe to determine the distribution of Semaphorin W mRNA expression. In this figure, E12, E15, E18, and P0 indicate the results for those samples at embryonic-days 12, 15, 18, and immediately after birth, respectively. The distribution among the CNS tissues (nine lanes at the left side) was obtained with those samples all at 6-weeks old. Fifteen $\mu$g of RNA was loaded in each lane. The upper panel shows the result of autoradiography. The positions corresponding to 18S and 28S ribosomal RNAs are indicated at the left margin of the panel. The lower panel shows the ethidium bromide staining of the gel. The upper and lower bands correspond 28S and 18S ribosomal RNAs, respectively.

Figure 3:
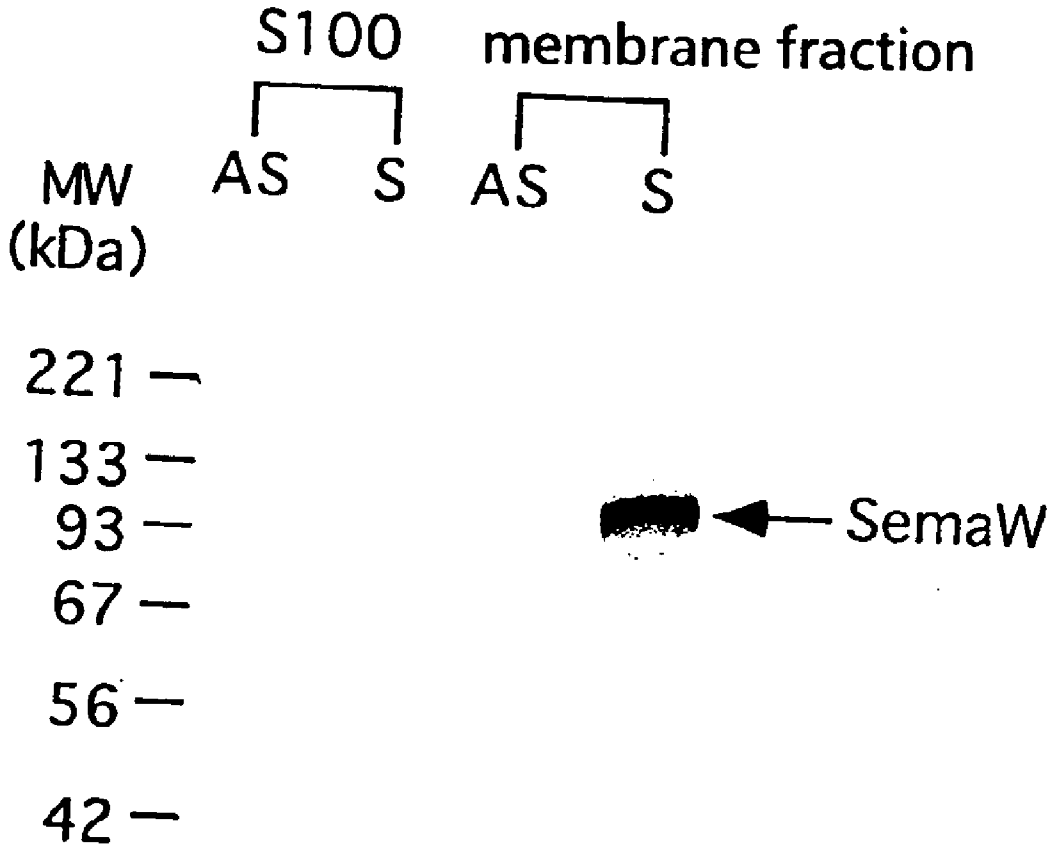

FIG. 3 shows a picture of electrophoresis indicating expression of Semaphorin W protein in COS 7 cells.

An expression plasmid for Semaphorin W (pUCSRα-rSWsense) was constructed, and introduced into COS 7 cells for transient expression (indicated as "S"). A plasmid containing Semaphorin W gene in the opposite direction (pUCSRα-rSWanti-sense) was used as control (indicated as "AS"). Three days after introducing plasmids, the cells were harvested, and the membrane fraction was prepared. The membrane fraction was fractionated by SDS-PAGE, and then subjected to Western blotting using an anti-Semaphorin W antibody. The antibody was obtained by immunizing rabbit with a partial peptide with the intracellular region of Semaphorin W Residues 710–730 of SEQ ID NO. 3 APPSGTTSYSQDPPSPSPEDE). The position of the band for Semaphorin W protein is indicated at the right margin of the figure. Positions and molecular weights of molecular weight makers are indicated in kilodaltons (kDa) at the left margin of the figure.

Figure 4:
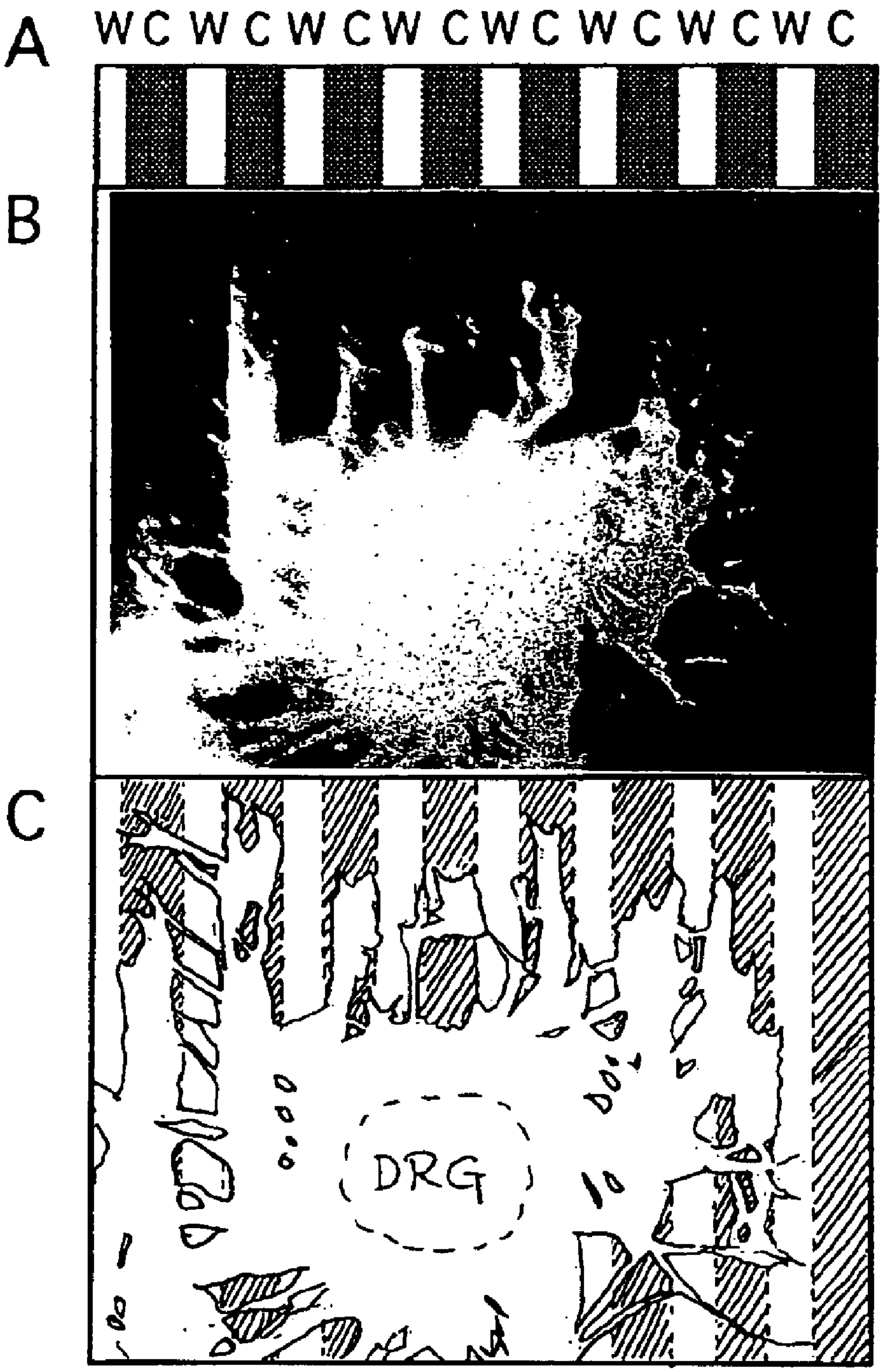

FIG. 4 shows a photomicrograph indicating that Semaphorin W inhibits neurite outgrowth.

A. The arrangement of membranes blotted on a polycarbonated filter. The membranes of COS cells containing Semaphorin W (W) and of control COS cells (C) were each blotted so that they formed the vertical stripes shown in the panel. The interval between the stripes was about 0.1 mm.

B. Subsequently, a dorsal root ganglion removed from chick embryo at embryonic-day 7 was placed on the membrane described above in A., incubated, fixed, stained, and then photographed under a fluorescence microscope. The white region corresponds to the neurites. C. A schematic representation of B. DRG indicate the position of the tissue piece of dorsal root ganglion. Another tissue piece can be seen at the left side. As apparent from this figure, the neurite outgrowth was inhibited on the membrane containing Semaphorin W.

Figure 5:
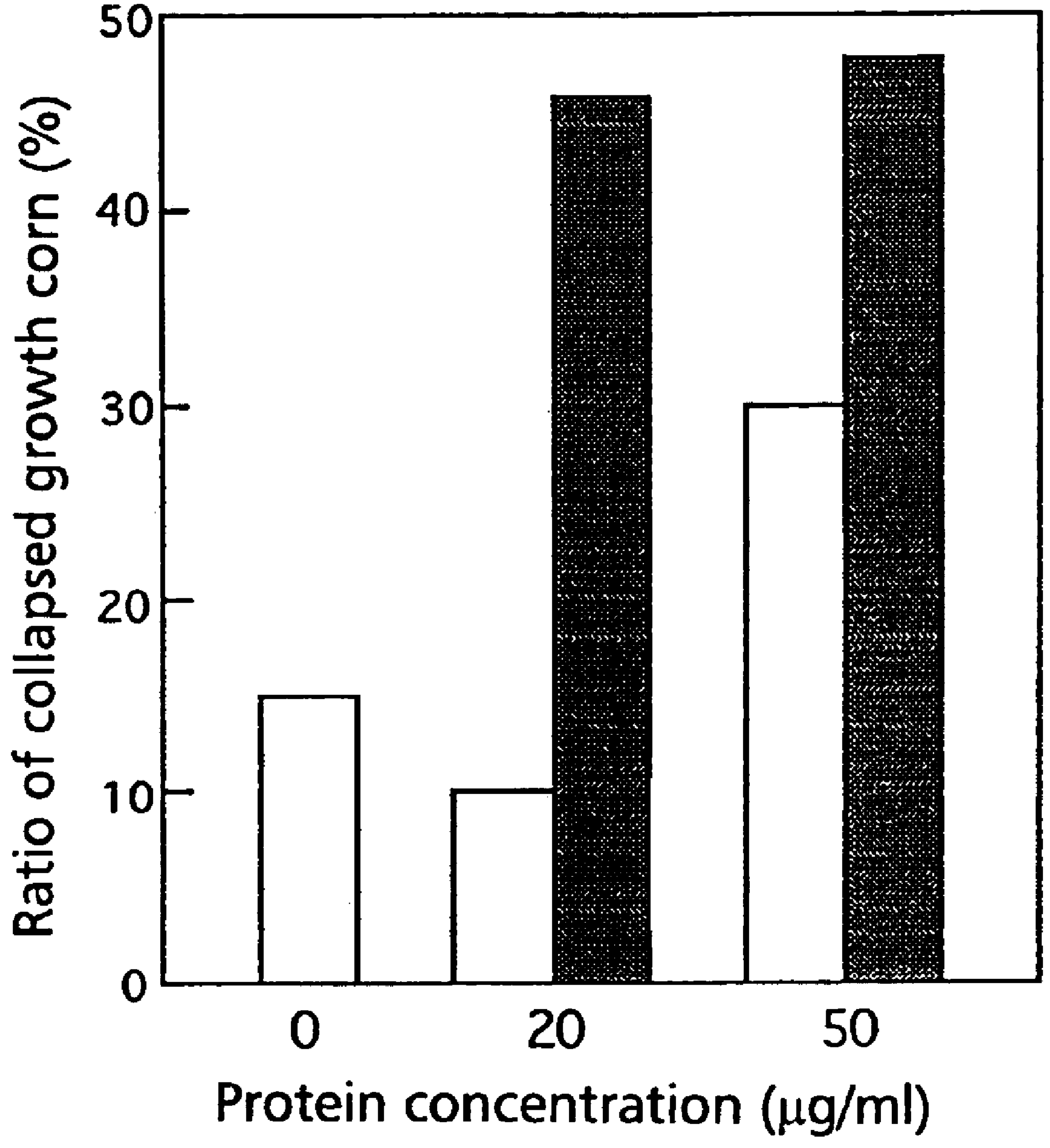

FIG. 5 is a graph indicating the growth-cone collapse activity of Semaphorin W. Retinal ganglion cells removed from chick embryo at embryonic-day 6 were cultured overnight, and a membrane extract (filled bars) prepared from COS cells transfected with a Semaphorin W-expressing plasmid or a membrane extract (unfilled bars) prepared from COS cells transfected with the vector alone was added at the final concentrations indicated on the horizontal axis of the graph. After culturing for additional 45 minutes, the cells were fixed, and the ratio (%; the vertical axis) of collapsed growth cone was measured under a microscope.

Figure 6:
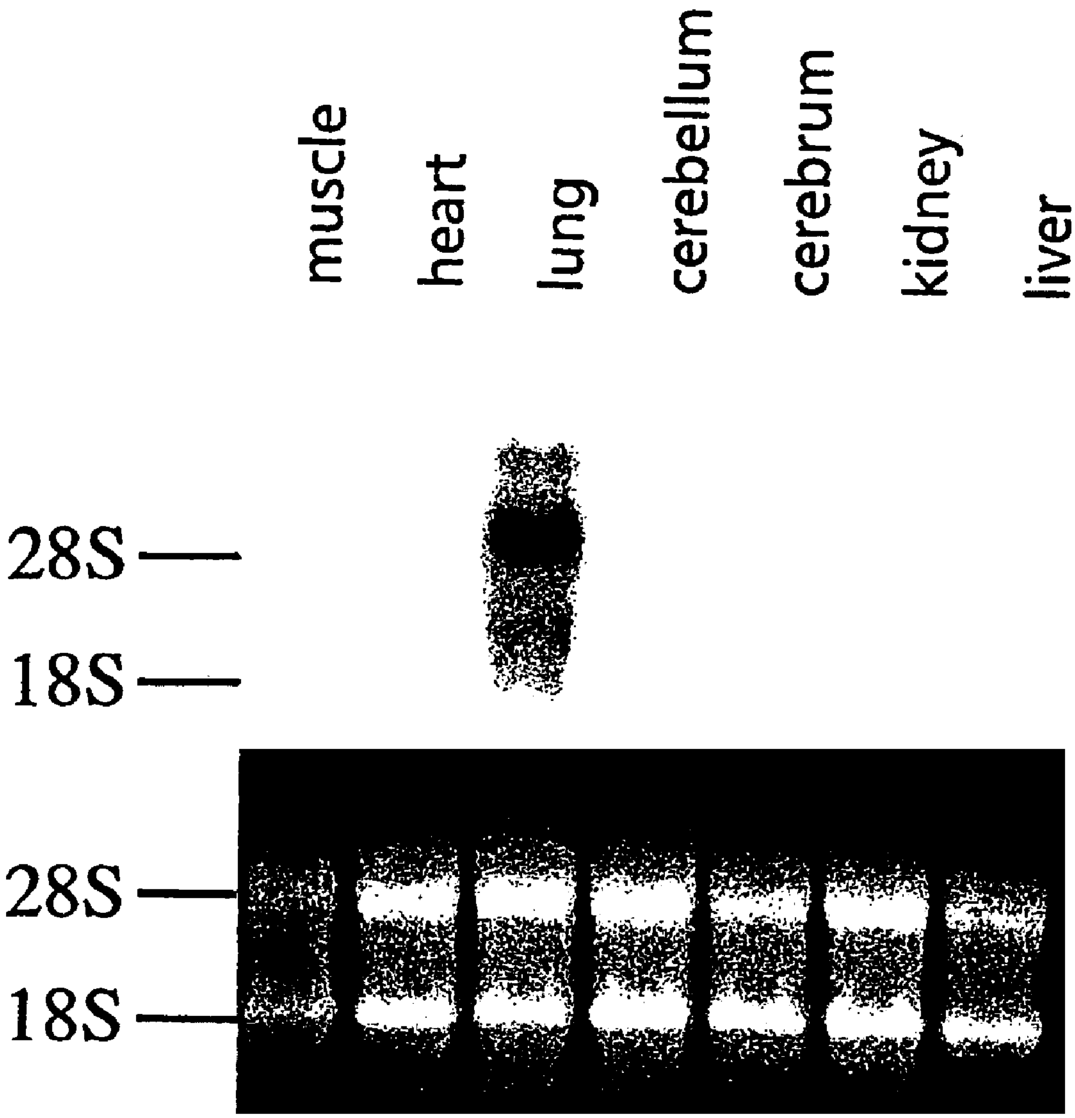

FIG. 6 shows a picture of electrophoresis indicating the in vivo distribution of Semaphorin III expression among various tissues determined by. Northern analysis.

Total RNAs were extracted from various tissues of adult rats, electrophoresed on 1% agarose-formamide gel, blotted onto a filter, and hybridized with $^{32}$P-labeled mouse Semaphorin III DNA probe to determine the distribution of Semaphorin III mRNA expression. Fifteen $\mu$g of RNA was loaded in each lane. The upper panel shows the result of autoradiography. The positions of 18S and 28S ribosomal RNAs are indicated at the left margin of the figure. The lower panel indicates the ethidium bromide staining of the gel. The upper and lower bands correspond to 28S and 18S ribosomal RNAs, respectively.

EXAMPLES

Fundamental procedures for experiments are described in detail in many publications such as "Molecular Cloning, 2nd Ed." edited by Maniatis et al. (Cold Spring Harbor Laboratory Press, 1989), "Current Protocols in Molecular Biology" edited by Ausubel et al., (John Wiley & Sons, 1987), and "Saibo-Kogaku-Jikken Protocols" edited by Department of Oncology, The Institute of Medical Science, The University of Tokyo (Shujunsha, 1991). The present invention is not intended to be limited by the following examples, and the examples may be of course modified as usual.

Example 1

Search Through Database for a Novel Semaphorin Gene

Using the dbEST database of the National Center for Biotechnology Research (Bethesda, Md., USA), DNA sequence which encodes an amino acid sequence well conserved in known Semaphorin genes was searched. As a result, T09073 proved to encode as a partial sequence, the sequence: Gln-Asp-Pro-Val-Cys-Ala-Trp (SEQ ID NO. 12) which is similar to the sequence consisting of seven amino acids extremely well conserved among known Semaphorin genes: Gln (or Arg)-Asp-Pro-Tyr-Cys-Ala (or Gly)-Trp (SEQ ID NO. 13). It was, however, impossible to conclude that the sequence is part of a novel Semaphorin gene, partly because this sequence consisting of 364 bp is so short and partly because the reading frame could not be determined due to the presence of undetermined bases. In addition, distribution of a gene containing this sequence was not known. Thus, the present inventors adopted the following strategy. Firstly, we confirmed by determining distribution of the gene expression that it is mainly expressed in the adult CNS in agreement with the aim of the present invention. The full length gene was then cloned in order to judge whether or not it corresponds to a novel Semaphorin gene.

Example 2

Distribution of Expression of Gene Containing T09073

Distribution of expression of a gene containing T09073 as a partial sequence was studied by Northern method. Although T09073 is presumed to be a human gene sequence since it has been submitted to the database as a sequence derived from a human child brain cDNA library, Northern analysis was carried out with rat samples in the light of the ease of the sample preparation. RNAs were prepared from various tissues of adult and fetal rats according to AGPC method (Takashi Tuji and Toshikazu Nakamura, *Jikken-Igaku*, vol. 9, 1991, pp. 1937–1940; M. F. Ausubel et al., ed., "Current Protocols in Molecular Biology", 1989, pp. 4.2.4–4.2.8, Greene Pub. Associates & Wiley-Interscience). Briefly, 10 ml of a denaturing solution (4M guanidine thiocyanate, 25 mM sodium citrate (pH 7.0), 0.5% sarkosyl, 0.1 M 2-mercaptoethanol) was added to each 1 g of excised tissues, and quickly homogenized using a Polytron homogenizer. To the homogenate, 0.1 volume of 2 M sodium acetate (pH 4.0), 1 volume of water-saturated phenol, and 0.2 volumes of chloroform-isoamyl alcohol (49:1) were added, and the mixture was vigorously stirred. After centrifugation, the aqueous layer was isolated, an equal volume of isopropyl alcohol was added thereto, and the mixture was allowed to stand at −20° C. for 1 hour. The precipitate was recovered by centrifugation, and dissolved again in 2–3 ml of the denaturing solution per 1 g tissue. An equal volume of isopropyl alcohol was added, and the mixture was allowed to stand at −20° C. for 1 hour, and then RNA was centrifuged. The precipitate was washed with 75% ethyl alcohol, dried briefly, and then dissolved in an appropriate amount of water.

Figure 1:
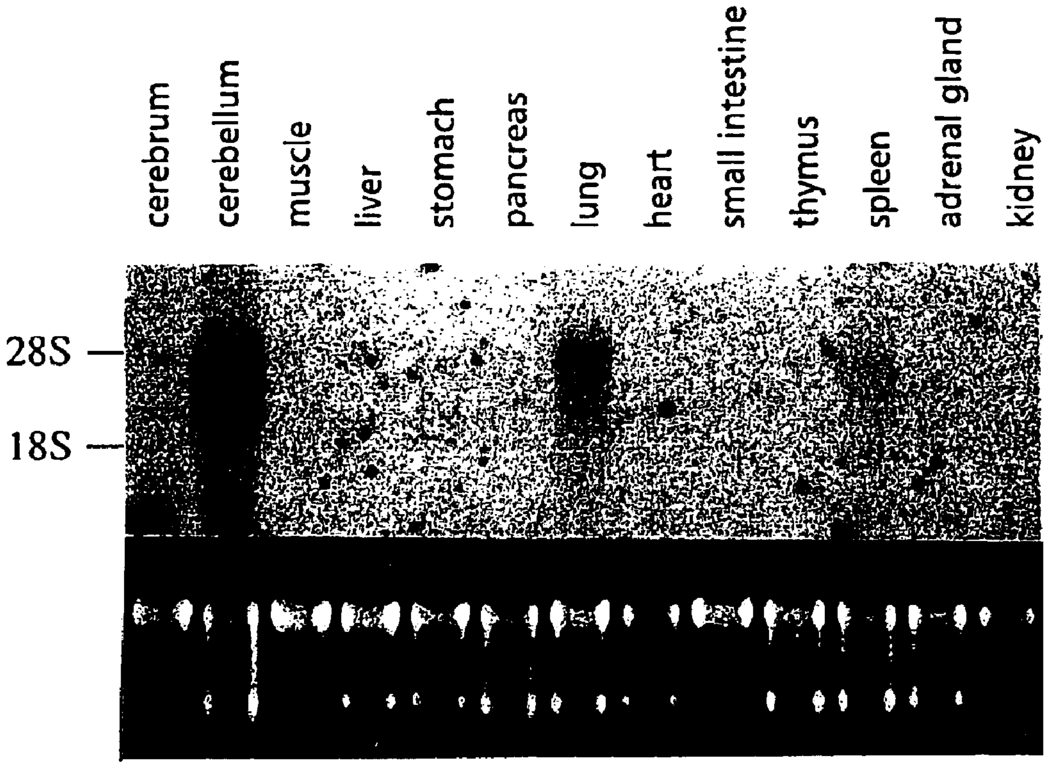
FIG. 1 shows a picture of electrophoresis indicating distribution of Semaphorin W expression among various tissues determined by Northern analysis.

Subsequently, electrophoresis and Northern blotting of RNAs were carried out by conventional methods described below. RNAs prepared from various tissues were firstly electrophoresed on 1% agaroseose gel containing formaldehyde. The gel was shaken in 50 mM NaOH for 20 min, and then in 10×SSPE (1×SSPE consists of 0.15 M sodium chloride, 10 mM sodium dihydrogenphosphate, and 1 mM ethylenediaminetetraacetic acid disodium salt, adjusted to pH 7.0) for 40 min. The RNAs were then blotted onto a nylon membrane (Biodyne B, Nippon Pall) by means of capillary transfer, and fixed using a UV cross-linker (Stratagene) (0.6 J/cm$^2$) for use in hybridization. As a probe, a DNA fragment consisting of 196 base pairs at the 5' region of T09073 was synthesized, and labeled with $^{32}$P using Megaprime DNA Labeling System (Amersham). Hybridization was carried out by placing the nylon membrane onto which RNAs were blotted and the probe DNA in the same hybridization buffer as that described above in (2) and allowing them to stand at 42° C. for 48 hours. After the reaction, the nylon membrane was washed 2–3 times in 2×SSPE, 0.5% (w/v) SDS at 42° C. for 10 min, and then 2–3 times in 2×SSPE, 0.5% SDS (w/v) at 55° C. for 10 min. Radioactivity on the membrane was then analyzed using BAS 2000 Bio-Imaging Analyzer. As shown in FIGS. 1 and 2, the results confirmed that the gene was widely expressed in the adult CNS tissues, whereas among the other tissues, it was expressed only in the lung and spleen of the adult throughout the fetal and postnatal periods. It was thus demonstrated that the gene exhibited a distribution of expression expected for a gene for CNS-neuron regeneration inhibitor.

Example 3

Cloning of Rat Semaphorin W Gene

In order to determine whether or not the above gene containing T09073 sequence actually corresponds to a novel Semaphorin gene, the inventors cloned the gene in full length using the 196 bp DNA fragment prepared in the above Example 2 as a probe, and determined the sequence. Because of the ease of sample preparation, the rat gene was firstly cloned. cDNA libraries were prepared by a conventional method described in the above-mentioned laboratory manual, using mRNAs prepared from rat brain and muscle by conventional procedures with Lambda Zap II (λZapII) cDNA Library Preparation Kit (Stratagene). About 150 thousand plaques were then generated on agarose plates using the cDNA library, and the plaques were transferred onto nylon membranes (Nippon Pall). After denaturing and neutralizing the DNAs, they were fixed with ultraviolet rays of 0.6 J/cm$^2$, and used in hybridization. The hybridization was carried out by placing the nylon membrane and the 196 bp DNA fragment labeled with $^{32}$P (prepared using Megaprime DNA Labeling System (Amersham) according to the manufacturers protocol) as a probe in a hybridization buffer (45% (v/v) formamide, 5×SSPE, 2× Denhardt's solution (Wako Pure Chemical Industries), 0.5% (w/v) SDS, 20 μg/ml salmon sperm DNA (Wako Pure Chemical Industries)) and allowing them to stand at 42° C. for 48 hours. After the reaction, the nylon membrane was washed 2–3 times in 2×SSPE, 0.5% (w/v) SDS at room temperature for 10 min, and then 2–3 times in 2×SSPE, 0.5% (w/v) SDS at 42° C. for 10 min. The filters thus prepared were analyzed using BAS 2000 Bio-Imaging Analyzer (Fuji Film), and six positive signals were obtained. Plaques located at the positions of the positive signals were excised from the agarose plates, placed in 500 μl of SM buffer (100 mM sodium chloride, 15 mM magnesium sulfate, 50 mM Tris, pH 7.6, and 0.01% gelatin) supplemented with 20 μl of chloroform, and left stand overnight at 4° C. to elute the phages. The recombinant lambda phages thus obtained were subjected to a secondary screening according to the same procedures as those described above, and single plaques were isolated. The phages thus obtained were treated in the following manner for in vivo excision of a phagemid containing the cDNA insert, according to the protocol of Stratagene. Agarose gels containing the four single plaques obtained in the secondary screening were each placed in 500 μl of SM buffer, supplemented with 20 μl of chloroform, and then allowed to stand overnight at 4° C. Two hundred fifty μl of the phage solution obtained, 200 μl of *E. coli* XL-1 Blue MRF' suspended in 10 mM magnesium chloride at $OD_{600}$=1.0, and 1 μl of ExAssist helper phage (>1×10$^6$ pfu/ml) were mixed, and incubated at 37° C. for 15 min. Then, 3 ml of LB medium (prepared by mixing 0.5% (w/v) sodium chloride, 1% (w/v) Bactotrypton (Difco); and 0.6% (w/v) yeast extract (Difco) followed by adjusting the pH to 7.0 with 5 M sodium hydroxide) was added, and the mixture was shaken at 37° C. for 2–3 hours. The cells were removed by centrifugation at 2000×g for 15 min, and the supernatant was heat-treated at 70° C. for 15 min. The supernatant was then centrifuged again at 2000×g for 15 min, and recovered as a stock solution of a phagemid containing the cDNA insert. An aliquot (10–100 μl) of the phagemid stock solution was mixed with 200 μl of *E. coli* SOLR ($OD_{600}$=1.0), incubated at 37° C. for 16 min. Then, 10–50 μl of the mixture was plated onto an ampicillin plate, and incubated overnight at 37° C. to obtain *E. coli* strain which contained the double-stranded phagemid into which the gene fragment of interest has been inserted.

The base sequence of the cDNA clone thus obtained was then analyzed on Perkin-Elmer Model 377 DNA Sequencer to determine the complete base sequence. The reaction was carried out using PRISM Dye termination kit (Perkin-Elmer). The DNA base sequence thus determined (4008 bases), the putative open reading frame (2331 bases), and the amino acid sequence (776 amino acids) are shown in SEQ ID NOs: 1, 2, and 3, respectively.

Since the gene encoded an amino acid sequence having a so-called semaphorin domain at positions 62 to 567, definitely confirming that the protein belongs to the Semaphorin family, it was designated Semaphorin W. In addition, the segment of T09073 consisting of 196 base pairs at its 6' terminus, used as a probe in Examples 2 and 3, proved to correspond to the base sequence from position 1661 to position 1756 (SEQ ID NO: 7) of Semaphorin W gene shown in SEQ ID NO: 1. Furthermore, the base sequence from position 1561 to position 1924 of Semaphorin W gene shown in SEQ ID NO: 1 had 87% identity with the whole sequence of T09073 consisting of 364 bp, it was confirmed for the first time that T09073 is a partial sequence of human Semaphorin W gene.

Example 4

Cloning of Human Semaphorin W

Human hippocampus and forebrain cDNA libraries purchased from Stratagene were screened as described in Example 3 using the full-length rat Semaphorin W cDNA cloned in Example 3 as a probe to obtain a clone #103. Determination of the base sequence of the clone #103 by the same procedures as those described in Example 3 revealed that this clone comprised the cDNA sequence consisting of 333 base pairs shown in SEQ ID NO: 10 at its 6' region and the cDNA sequence consisting of 2315 base pairs shown in SEQ ID NO: 4 at its 3' region. In these sequences, all the base sequence shown in SEQ ID NO: 10 and the segment of the base sequence shown in SEQ ID NO: 4 from position 1 through position 1761 (SEQ ID NO: 5) are presumed to be parts of an open reading frame. The base sequence shown in SEQ ID NO: 10 could be thus translated into a peptide consisting of contiguous 111 amino acids (SEQ ID NO: 11), and the base sequence shown in SEQ ID NO: 5 could be translated into a peptide consisting of contiguous 587 amino acids (SEQ ID NO: 6). Since these amino acid sequence had 82% (SEQ ID NO: 11) and 92% (SEQ ID NO: 6) identities to the sequences at the corresponding region in rat Semaphorin W, it was definitely confirmed that they are parts of human Semaphorin W gene. In addition, the sequence T09073 found in the EST database corresponded to a partial sequence of clone #103 from position 922 to position 1285 in SEQ ID NO: 4, and within this region the base sequences were 98% identical to each other.

*E. coli* strain SOLR (hSW103), a transformant obtained by introducing a plasmid hSW103, which incorporates the insert of the above clone #103 (a region corresponding to cDNA for human Semaphorin W) in a vector pBluescript, into *E. coli* strain SOLR, has been deposited at the National Institute of Bioscience and Human Technology (1-1-3 Higashi, Tsukuba, Ibaraki, Japan) under Deposit No. FERM BP-6089 on Aug. 29, 1997.

Example 5

*E. Coli* Expression and Purification of Partial Protein of Semaphorin W.

The intracellular domain of Semaphorin W (the part corresponding to position 687 through position 776 of the amino acid sequence shown in SEQ ID NO: 3) was expressed in *E. coli* cells, and purified.

A 310 bp fragment encoding the sequence of the intracellular domain was firstly obtained by carrying out PCR under usual conditions using two primers, 5'-GATAAGGATCCGGGTCGCCGTCAGCAGCGT-3' (SEQ ID NO: 8) and 5'-GGCTGGAATTCATTTTCCCCGGCTTTA-3' (SEQ ID NO: 9), with Semaphorin W cDNA (SEQ ID NO: 1) as a template. This fragment was then cleaved with restriction enzymes BamHI and EcoRI, and incorporated into an expression plasmid pRSETB (Invitrogen) which had been also cleaved at BamHI and EcoRI sites to obtain an expression plasmid pRSWinc.

The plasmid pRSWinc thus obtained was used to transform *E. coli.* strain BL21(DE3)pLysS (Stratagene), and the cells were cultured overnight on LB plate containing 50 μg/ml ampicillin to obtain transformants. By analyzing the base sequence of a plasmid prepared from the transformant, it was confirmed that the transformant carried a plasmid having the desired structure. The transformant thus obtained was cultured with shaking in LB broth containing 50 μg/ml ampicillin. When $OD_{600}$ of the culture reached 0.5, IPTG was added at a final concentration of 1 mM, and the cells were further cultured overnight. The culture medium was then centrifuged at 5000×g for 15 min to harvest the cells. All proteins of the harvested cells were analyzed by SDS-PAGE, and it was confirmed that a protein having an expected molecular weight was produced.

The Sema W partial protein expressed in *E. coli* cells was then affinity-purified by taking advantage of affinity between the His tag at the amino terminus of this protein and a nickel-Sepharose. This procedure is described in detail in the protocol supplied by Qiagen. Briefly, Sema W protein was expressed in *E. coli* cells as described above, and 5 ml of Solution A (6M guanidine-HCl, 0.1 M sodium phosphate, 0.01 M Tris-HCl, pH=8.0) was added to each 1 g of the cell. The cells were suspended well in the solution, and then stirred at room temperature for more than 1 hour to be solubilized. Subsequently, this protein solution was mixed with Ni-NTA resin (Qiagen) pre-equilibrated with Solution A, gently stirred at room temperature for more than 2 hours to allow the binding of proteins to the resin, and the resin was then packed into a column. The column was washed with 10 volumes of Solution A, then with 5 volumes of Solution B (8M urea, 0.1 M sodium phosphate, 0.01 M Tris-HCl, pH=8.0), and further with 5 volumes of Solution C (8M urea, 0.1 M sodium phosphate, 0.01 M Tris-HCl, pH=6.3) to elute the bound proteins. During the elution, the eluate was collected in one column volume fractions, and subjected to SDS-PAGE to check the proteins eluted. The desired fractions were then concentrated, and stored at −20° C. until use.

The N-terminal amino acid sequence of the protein thus obtained was analyzed to confirm that it was the desired protein. This partial protein of Semaphorin W can be used, for example, as an antigen in producing antibodies.

Example 6

Production of Anti-Semaphorin W Antibody

In order to produce anti-Semaphorin W antibodies, a polyantigenic peptide having the N- and C-terminal sequences of rat Semaphorin W, ALTLPFSGERPRRID (residues 92–106 of SEQ ID NO: 3) and APPSGTTSYSQD-PPSPSPEDER (residues 710–731 of SEQ ID NO: 3), was synthesized by a conventional method (Seikagaku, vol. 63 (1991) pp. 1345–1348), and used to immunize a rabbit. Immunization of rabbit was achieved according to conventional procedures. Specifically, 0.4 mg of the antigen was mixed with Freund's complete adjuvant, and used to immunize a rabbit subcutaneously. Subsequently, the rabbit was further subcutaneously immunized 4 times at 2 weeks intervals with 0.2 mg of the antigen mixed with Freund's incomplete adjuvant. One week after the last immunization, whole blood was collected from the rabbit. Purification was then carried out by a conventional method using a protein A column to obtain a purified monoclonal antibody. It was concluded that the antibody obtained was an anti-Semaphorin W antibody properly recognizing Semaphorin W protein, because of the reasons, for example, that this antibody recognized a protein having a molecular weight expected for Semaphorin W in Western blotting as described below in Example 7, that when Semaphorin W having a myc tag attached thereto was immunoprecipitated with an anti-myc antibody, the protein recognized by this antibody was also co-precipitated, and that both of an antibody produced using a N-terminal peptide as an antigen and an, antibody produced using a C-terminal peptide as an antigen recognized a protein having the same molecular weight.

Example 7

Expression of Semaphorin W in animal cells A DNA fragment encoding Myc tag having the sequence Asp-Ile-Gly- Gly-Glu-Gln-Lys-Lue-Ile-Ser-Glu-Glu-Asp-Leu (SEQ ID NO: 14) was inserted just before the stop codon of rat Semaphorin W gene shown in SEQ ID NO: 1, and the recombinant gene was introduced into an expression plasmid pUCSRα(pUCSRα-rSWMYC).

This expression plasmid containing Semaphorin W gene was then introduced into COS 7 cells according to conventional procedures, and the cells were harvested after 3 days in order to prepare the membrane fraction in the following manner. The cells were harvested using a cell scraper, and the harvested cells were homogenized in the presence of protease inhibitors. The homogenate was separated into precipitate and supernatant by high-speed centrifugation at 12,000 g for 10 min. The supernatant was further subjected to ultracentrifugation at 100,000 g for 30 min, and the soluble fraction was recovered as the cytoplasmic fraction (S100). The cytoplasmic fraction obtained was stored at −80° C. until use. On the other hand, the precipitate from the above high-speed centrifugation was washed twice with the homogenizing solution, suspended in 2 volumes of 2.25 M sucrose/PBS, and overlaid onto 2.25 M sucrose/PBS. After 0.8 M sucrose/PBS was further overlaid onto the top, it was centrifuged at 12,000 g for 20 min. The membrane fraction was recovered from the lower interface, then washed twice with the homogenizing solution, and stored at −80° C. until use.

The membrane and cytoplasmic fractions thus obtained were each separated by SDS-PAGE, and then subjected to Western blotting in a conventional manner using anti-Myc antibody 9E10 (Calbiochem). An alkali phosphatase-labeled anti-mouse IgG antibody (Biosource) was used as the secondary antibody. In the Western blotting, a specific band was observed at the position corresponding to about 110 kDa only when the plasmid containing Semaphorin W gene was introduced, confirming that the Myc-tagged rat Semaphorin W protein was expressed in COS cells and existed in the membrane.

Similarly, another membrane fraction was prepared using an expression plasmid for Semaphorin W having no Myc tag (pUCSRα-rSWsense), and subjected to Western blotting as above using the anti-Semaphorin W antibody produced in Example 6. As a result, a specific band of about 100 kDa was recognized, confirming that Semaphorin W protein was expressed in COS cells and existed in the membrane in consistent with the above result (FIG. 3).

Example 8

Effect of Semaphorin W on neurite outgrowth A stripe assay was carried out in order to evaluate the effect of Semaphorin W on neurite outgrowth. The method of stripe assay is described in detail in literature (*Development* 101, 685–696 (1987)). Briefly, an expression plasmid for Semaphorin W was firstly introduced into COS cells as described above in Example 7, and the membrane fraction was prepared from the COS cells expressing Semaphorin W on their cell membrane. In parallel, another membrane fraction was also prepared in the same manner from COS cells not expressing Semaphorin W (that is, COS cells transfected with a vector carrying no Semaphorin gene) as a control. The membrane fractions obtained were blotted onto a micropore polycarbonated filter (Coaster) using a silicone matrix striped with slits so as to form alternating stripes each having a width of about 0.1 mm. The filter was then transferred into a neuron culture medium (F12, 10% FCS, 20 ng/ml NGF), and a dorsal root ganglion removed by a conventional method from chick embryo at embryonic-day 7 was carefully placed on the filter, and cultured in a $CO_2$ incubator at 37° C. for 48 hours. After completion of the cultivation, the cells were fixed with 1% glutaraldehyde. DiI (Molecular Probe) was then inserted with caution into the dorsal root ganglion, and the filter was incubated in PBS (−) at 37° C. for 2 to 3 days. Subsequently, elongation of neurite outgrowing from the dorsal root ganglion on the membrane containing Semaphorin W was compared with that on the control membrane to evaluate the effect of Semaphorin W on neurite outgrowth. The result thus obtained is shown in FIG. 4. In the figure, "W" indicates the regions onto which the membrane of COS cells containing Semaphorin W was blotted, and "C" indicates the regions onto which the membrane of control COS cells was blotted. The neurites appear in white because they were stained with DiI. As can be seen at a glance, it was demonstrated that neurite outgrowth was inhibited on the cell membrane containing Semaphorin W. In living bodies, Semaphorin W is widely expressed in CNS of the adult (Example 2), and therefore, neurite outgrowth in the CNS is believed to be inhibited.

Example 9

Growth-Cone Collapse Activity of Semaphorin W

In order to determine whether or not Semaphorin W has a growth-cone collapse activity, retinal ganglion cells were cultured as described below, and the morphological change of growth cone was evaluated following addition of Semaphorin W protein solubilized from the membrane fraction using a surfactant.

Specifically, retinal ganglion removed from chick embryo at embryonic-day 6 was placed on a dish coated with polylysine and laminin by a conventional method, and cultured overnight in a medium (F12, 10% FCS, 20 ng/ml BDNF) in a $CO_2$ incubator at 37° C. Next day, a membrane fraction prepared as described above in Example 7 was solubilized with a surfactant, added to the medium, and further incubated for 30 min to one hour. Subsequently, the sample was fixed with 1% glutaraldehyde, and the morphological change of the growth cone was observed. In this procedure, the membrane fraction may be solubilized, for example, according to the method described in literature (*Cell* 75, 217–227 (1993)). Specifically, COS cells transfected with an expression plasmid for Semaphorin W and expressing Semaphorin W, and COS cells transfected with a control vector plasmid and not expressing Semaphorin W were used as row materials, and the cell membrane fractions prepared as described above in Example 7 were each solubilized with 1–2% CHAPS, and then dialyzed against F12 to remove CHAPS. After centrifuging the dialyzed material to remove insoluble, the protein concentration was measured by a conventional method using BCA kit (Pierce), and used in the above measurement of growth-cone collapse activity. All the preparations were carried out in practice at 4° C.

As shown in FIG. 5, the results indicated that collapse of growth cone was observed at a rate 1.6- to 4.6-fold higher than the control when the extract of COS cells transfected with the Semaphorin W expressing plasmid was added. Accordingly, Semaphorin W is believed to have a neurite-outgrowth inhibition activity on retinal ganglion cells which are CNS-neuron.

Reference Example 1

Identification of the Site Essential to the Semaphorin Activity Using Semaphorin III PCR was conducted on the basis of the sequence information on Semaphorin III described in *Neuron,* 14, 941–948 (1995), and the structural gene of Semaphorin III was incorporated into an expression plasmid pUCSRα. The expression plasmid was then introduced into COS 7 cells by DEAE-dextran method. After 2 days, the Semaphorin III activity contained in the culture supernatant was determined by a method similar to that described in *Cell,* 75, 217–227 (1993), using the growth-corn collapse activity on chick dorsal root ganglion cells as an indicator. As a result, one clone which did not exhibit any activity was found. The base sequencing of the clone revealed that aspartic acid residue at position 198 was substituted by glycine. When compared with other known animal Semaphorins, the regions before and after the position 198 were not markedly conserved, although the position corresponding to aspartic acid residue was highly conserved among Semaphorins with a few exceptions in which glutamic acid residue was located at that position. This suggested that the aspartic acid residue is essential to expression of the activity. The gene was then subjected to site-directed mutagenesis by a conventional method to replace the glycine residue with aspartic acid. Since this mutagenesis restored the strong collapse activity, it was confirmed that all of the regions in the expression plasmid normally function except for that position. In conclusion, the aspartic acid at position 198 of Semaphorin III appears essential for the expression of the Semaphorin function. The amino acid residue corresponding to this aspartic acid residue is glutamic acid residue at position 204 in the amino acid sequence of Semaphorin W shown in SEQ ID NO: 3.

Reference Example 2
Tissue-Specific Gene Expression of Semaphorin III Determined by Northern Analysis To determine the distribution of Semaphorin III gene expression among mouse tissues, RNAs were prepared from various adult mouse tissues, and subjected to Northern analysis. The procedures for preparation, blotting, and hybridization of RNA were the same as those described in Example 2. The 560 bp MspI fragment of mouse Semaphorin III DNA described in Reference example 1 was used as a probe. As a result, it was demonstrated as shown in FIG. 6 that the expression of Semaphorin III in the adult is extremely high in the lung which is peripheral, while it is rather low in the CNS.

EFFECTS OF THE INVENTION

The present invention provides Semaphorin W inhibiting neurite outgrowth, and a gene therefor, as well as other Semaphorins hybridizing to said Semaphorin W gene, modified proteins or partial peptides of said Semaphorin W, antibodies against said Semaphorin W, antisense nucleotides against said Semaphorin W gene, and the use of such substances as pharmaceutical or diagnostic agents or laboratory reagents. The present invention further provides a method of screening for Semaphorin W antagonists employing said Semaphorin W, Semaphorin W antagonists obtained by said screening method, pharmaceutical agents comprising such antagonists, and transgenic animals regarding said Semaphorin W.

What is claimed is:

1. An isolated nucleic acid molecule comprising a polynucleotide having a nucleotide sequence selected from the group consisting of:

(a) the nucleotide sequence of SEQ ID NO:1;

(b) the nucleotide sequence of SEQ ID NO:2; and (c) a nucleotide sequence encoding the amino acid sequence of SEQ ID NO:3.

2. An isolated nucleic acid molecule comprising a polynucleotide having a nucleotide sequence selected from the group consisting of:

(a) the nucleotide sequence of SEQ ID NO:5; and (b) the nucleotide sequence of SEQ ID NO:10;

wherein said polynucleotide specifically hybridizes with a complement of a polynucleotide having a nucleotide sequence selected from the group consisting of:

(a) the nucleotide sequence of SEQ ID NO:1; and (b) the nucleotide sequence of SEQ ID NO:2;

under conditions of a buffer comprising 45%(v/v) formamide, 5×SSPE, at 42° C., and washing after hybridization with a buffer comprising 2×SSPE at 42° C., and said polynucleotide encodes a protein having the biological activity of inhibiting neurite outgrowth from dorsal root ganglion cells.

3. An isolated nucleic acid molecule comprising a polynucleotide having a nucleotide sequence selected from the group consisting of:

(a) the nucleotide sequence of SEQ ID NO:5; and (b) the nucleotide sequence of SEQ ID NO:10;

wherein said polynucleotide specifically hybridizes with a complement of a polynucleotide having a nucleotide sequence selected from the group consisting of:

(a) the nucleotide sequence of SEQ ID NO:1; and (b) the nucleotide sequence of SEQ ID NO:2;

under conditions of a buffer comprising 45%(v/v) formamide, 5×SSPE, at 42° C., and washing after hybridization with a buffer comprising 2×SSPE, at 42° C.;

and said polynucleotide encodes a protein having the biological activity of collapsing growth cones of retinal ganglion cells.

4. An expression plasmid comprising the nucleic acid molecule of claim 1, 2 or 3.

5. A host cell comprising the expression plasmid of claim 4.

6. A process for producing a recombinant protein, comprising culturing the host cell of claim 5 under conditions sufficient for the production of said protein and recovering said protein.

* * * * *

SEQUENCE LISTING

```
<160> NUMBER OF SEQ ID NOS: 15

<210> SEQ ID NO 1
<211> LENGTH: 4008
<212> TYPE: DNA
<213> ORGANISM: Rattus norvegicus
<220> FEATURE:
<221> NAME/KEY: 5'UTR
<222> LOCATION: (1)..(75)
<220> FEATURE:
<221> NAME/KEY: misc_feature
<222> LOCATION: (76)..(2406)
<223> OTHER INFORMATION: Coding region
<220> FEATURE:
<221> NAME/KEY: 3'UTR
<222> LOCATION: (2407)..(3977)
<220> FEATURE:
<221> NAME/KEY: polyA_signal
<222> LOCATION: (3978)..(4008)
<220> FEATURE:
<221> NAME/KEY: misc_feature
<222> LOCATION: (1)..(4008)
<223> OTHER INFORMATION: strandedness: double

<400> SEQUENCE: 1

gccgaggccc gcgcagtagc ggtactaagt agaggctgct ggacgcgccc cacccggcac      60

caggcggagc cagagatgct tgccagggcc gagcggcccc gcccgggccc ccggccgcct     120

ccggtctttc ccttcccgcc gccgctgtcg ctgctgctgc tgctggcgat actaagcgcc     180

ccggtgtgcg gccgcgtccc ccgctcagtg cccagaacct cgctgcccat ctccgaggct     240

gactcctatc tcacccggtt tgcagcgtct catacgtaca attactctgc tctccttgtg     300

gatcctgcct cccacacact ttacgtcggt gcacgggata gcatcttcgc tttaaccctc     360

cccttctctg gggaaagacc ccgaaggatc gactggatgg tacctgagac tcacagacag     420
```

-continued

```
aactgcagga agaaaggcaa gaaagaggac gaatgtcaca attttatcca gattctcgcc    480
attgtcaatg cctctcacct cctcacgtgc ggcaccttcg cttttgatcc gaagtgcggg    540
gttattgatg tgtccagttt ccagcaggtt gaaagacttg agagcggccg ggggaaatgt    600
ccttttgagc cagctcaacg gtcagcagct gtaatggctg gggcgtcct ctacaccgcc    660
actgtgaaga acttcctggg gactgagccc atcatctccc gagctgtggg tcgagctgag    720
gactggattc gaacagagac cttgtcatcc tggcttaatg ctccagcctt tgtcgcagct    780
atggtcctga gcccagctga gtggggggat gaagatggag acgatgaaat cttttttttc    840
ttcacggaga cctcccgagt gttggactcc tatgagcgca tcaaggtccc aagagtggcc    900
cgagtgtgtg cgggggacct tgggggcagg aagacccttc agcagagatg gacgacgttt    960
ctgaaggctg acctgctgtg cccagggccc gagcatggcc gggcctccgg ggttctgcag   1020
gctatggcag agcttcggcc tcagcctgga gcgggaaccc ccatctttta tgggatcttt   1080
tcctcccagt gggaaggagc tgccatctct gctgtgtgtg ccttccgacc ccaagacatc   1140
cgggcagtgc tgaatggtcc ctttagagag ctaaaacatg actgcaacag gggactgcct   1200
gtcatggaca acgaggtgcc ccagcccaga cctggagagt gcatcgccaa caacatgaag   1260
ctccagcagt ttggatcctc actctccctg ccagaccgcg tgctcacctt tatcagagac   1320
caccctctca tggacaggcc cgtgttcccg gctgacggcc gccccctgct ggtcactaca   1380
gatacagcct atctcagagt cgtggcccac agggtgacca gcctctcagg gaaagaatat   1440
gacgtgctct acctggggac agaggatgga cacctccacc gggctgtgcg cattggagct   1500
cagctcagtg tcttggagga tctggccttg ttcccagaac cacagccggt tgagagcatg   1560
aaattgtacc acgattggct cctggtgggc tcccatactg aggtgacaca agtgaacacc   1620
agcaactgtg gccgtctcca gagctgctcg gagtgtatcc tggcccagga ccccgtgtgc   1680
gcctggagct tccggcttga tgcttgtgtg gcccacgccg gcgagcaccg cgggatggtt   1740
caagatatag agtcagcgga tgtctcttct ttgtgtccaa aagaacctgg agaacatccc   1800
gtagtgtttg aagttccggt ggctactgtg ggccacgtgg tcctgccatg ttcccccagt   1860
tctgcctggg catcctgtgt gtggcaccag cccagtggag tgactgcgct cactccccgg   1920
agggatggac tagaggtggt ggtgacccca ggggccatgg gggcttatgc ttgcgagtgt   1980
caggagggtg gagccgcccg cgtggtggct gcttatagct tggtgtgggg cagccagcgg   2040
ggaccctcaa accgggccca caccgttgtg gggctggat tggttggctt tctcctgggt   2100
gttcttgcag catccctcac tctcctcctg attggtcgcc gtcagcagcg tcggcgacag   2160
agggagcttc tagctagaga caaggtgggc ttagatctgg gggctccacc ttctgggacc   2220
acaagctata gtcaggaccc tccctctcct tcgcctgaag atgaacggct gcccctggcc   2280
ctgggtaagc ggggcagtgg ttttggtggc ttccctccac ccttcctgct ggattcttgc   2340
ccaagcccag cccacatccg gctcactggg gcgcctctag ccacgtgtga tgagacctcc   2400
atctaaagcc ggggaaaatg actgccagcc atgagcagtc tctggaacta gtggctacca   2460
agaccatgat catggctgct cctttctctt ggagtctgtg tgttcacaca ttagtgtctg   2520
tcctctggac ctggacctgg cctttgccca gattcctgat tctcatgaga gatcaaccct   2580
gtaaccttct gcgatggcct cttgtcttgg gcccatcagc ttgtggggtg gagtaaggac   2640
ataggccccg gaaagggaat cagtgtggag gtagttgggg cgtgtgtgcc ctgcgtcctt   2700
gtggtggctg tatgatttcc cagtctgctg actctgggga gcgcatgatc ccctgactgc   2760
```

-continued

```
cttgagatct ctcccaactc agtttcccct tgctctggaa gagtgtgtgt ctatacactg   2820

gtgtgcctag aaggcctgtc catgtgtgca tggacgacag ggccggtgcc tcggtgcttt   2880

tggggagtcg gagagaaagg ttggaatggg ggacaactta accctcggta gccagtgagg   2940

gaaaccacat gcccgtcccc atcaccccac agcgcttctt taactttgag caaagttccc   3000

aaagtgacct tctgggtggg aagggcagca ggacatgtgg cccccgtcct tctccttgtc   3060

tttcccttct ggctgccaac cactgccgtg ccaccgctgc gctttccctg gctggagtgg   3120

aggctgagtc ctctgtcctt ggtttccatt taaaatgaac ttcacaacat tctaaatatt   3180

gggggatgac aaatgacttt tttccccaga aaagtgtgta ggaaatacaa gcaggttaaa   3240

gaagatttgc ctcagtgact ttcacccttg ccctaaagca ggagtccctc agctagcgtc   3300

tgtggactcc ctgaaattgt atgcgtctgt ggactccctg aaattgtatg caaagtgtct   3360

gtgtgtgtgt gtgtgtgtgt gtgtgtgtgt gtgtgtgtgt gtttgcgtgc atgtgtgcat   3420

gtgtgtttga tggctttcat cagattctca aggccttaat gaggttaaag gaccacggcc   3480

tatagtcacc acacttgggc cacatggagg aggtgttgct ctctgaggca gttcctccct   3540

ggcctgcctg aggccagccc ctggacacat tgctgctgga gaccccacat ctctccagaa   3600

cttggaagct aggctctgcg cgtgcttgaa ggcaccacca tctcccttct tgcttcattc   3660

tcctgtgtgc tctgcctctg ctcagtcctg ctcttggcct gtgaatgtgc ctcgcccgtc   3720

cctggtgggg gacctcaaac cccagtgctg atgctaccct ttccagtggg agtttctgtt   3780

ctgctttcct tgacagcagc ctgtgaacta ctcacgagtc cccttggttt ggagttcccg   3840

gtggctttga gtaggatctt tggcgtggca tctaacctag cagcattgat cgttcattgt   3900

aaagtgggga tatacctacc tcagggttgc tgcaaggatc aaacgaggaa acgtataaat   3960

aaagcattac ccacagcaaa aaaaaaaaaa aaaaaaaaaa aaaaaaaa                4008
```

```
<210> SEQ ID NO 2
<211> LENGTH: 2331
<212> TYPE: DNA
<213> ORGANISM: Rattus norvegicus
<220> FEATURE:
<221> NAME/KEY: misc_feature
<222> LOCATION: (1)..(2331)
<223> OTHER INFORMATION: Coding region
<220> FEATURE:
<221> NAME/KEY: misc_feature
<222> LOCATION: (1)..(2331)
<223> OTHER INFORMATION: strandedness: double

<400> SEQUENCE: 2

atgcttgcca gggccgagcg gccccgcccg ggcccccggc cgcctccggt ctttcccttc     60

ccgccgccgc tgtcgctgct gctgctgctg gcgatactaa gcgccccggt gtgcggccgc    120

gtcccccgct cagtgcccag aacctcgctg cccatctccg aggctgactc ctatctcacc    180

cggtttgcag cgtctcatac gtacaattac tctgctctcc ttgtggatcc tgcctcccac    240

acactttacg tcggtgcacg ggatagcatc ttcgctttaa ccctcccctt ctctggggaa    300

agaccccgaa ggatcgactg gatggtacct gagactcaca gacagaactg caggaagaaa    360

ggcaagaaag aggacgaatg tcacaatttt atccagattc tcgccattgt caatgcctct    420

cacctcctca cgtgcggcac cttcgctttt gatccgaagt gcggggttat tgatgtgtcc    480

agtttccagc aggttgaaag acttgagagc ggccgggggga aatgtccttt tgagccagct   540

caacggtcag cagctgtaat ggctgggggc gtcctctaca ccgccactgt gaagaacttc    600

ctggggactg agcccatcat ctcccgagct gtgggtcgag ctgaggactg gattcgaaca    660
```

-continued

```
gagaccttgt catcctggct taatgctcca gcctttgtcg cagctatggt cctgagccca    720
gctgagtggg gggatgaaga tggagacgat gaaatctttt ttttcttcac ggagacctcc    780
cgagtgttgg actcctatga gcgcatcaag gtcccaagag tggcccgagt gtgtgcgggg    840
gaccttgggg gcaggaagac ccttcagcag agatggacga cgtttctgaa ggctgacctg    900
ctgtgcccag ggcccgagca tggccgggcc tccggggttc tgcaggctat ggcagagctt    960
cggcctcagc ctggagcggg aaccccccatc ttttatggga tcttttcctc ccagtgggaa   1020
ggagctgcca tctctgctgt gtgtgccttc cgaccccaag acatccgggc agtgctgaat   1080
ggtcccttta gagagctaaa acatgactgc aacaggggac tgcctgtcat ggacaacgag   1140
gtgccccagc ccagacctgg agagtgcatc gccaacaaca tgaagctcca gcagtttgga   1200
tcctcactct ccctgccaga ccgcgtgctc acctttatca gagaccaccc tctcatggac   1260
aggcccgtgt tcccggctga cggccgcccc ctgctggtca ctacagatac agcctatctc   1320
agagtcgtgg cccacagggt gaccagcctc tcagggaaag aatatgacgt gctctacctg   1380
gggacagagg atggacacct ccaccgggct gtgcgcattg gagctcagct cagtgtcttg   1440
gaggatctgg ccttgttccc agaaccacag ccggttgaga gcatgaaatt gtaccacgat   1500
tggctcctgg tgggctccca tactgaggtg acacaagtga acaccagcaa ctgtggccgt   1560
ctccagagct gctcggagtg tatcctggcc caggaccccg tgtgcgcctg gagcttccgg   1620
cttgatgctt gtgtggccca cgccggcgag caccgcggga tggttcaaga tatagagtca   1680
gcggatgtct cttctttgtg tccaaaagaa cctggagaac atcccgtagt gtttgaagtt   1740
ccggtggcta ctgtgggcca cgtggtcctg ccatgttccc ccagttctgc ctgggcatcc   1800
tgtgtgtggc accagcccag tggagtgact gcgctcactc cccggaggga tggactagag   1860
gtggtggtga ccccaggggc catgggggct tatgcttgcg agtgtcagga gggtggagcc   1920
gcccgcgtgg tggctgctta tagcttggtg tggggcagcc agcggggacc ctcaaaccgg   1980
gcccacaccg ttgtgggggc tggattggtt ggctttctcc tgggtgttct tgcagcatcc   2040
ctcactctcc tcctgattgg tcgccgtcag cagcgtcggc gacagaggga gcttctagct   2100
agagacaagg tgggcttaga tctgggggct ccaccttctg ggaccacaag ctatagtcag   2160
gaccctccct ctccttcgcc tgaagatgaa cggctgcccc tggccctggg taagcggggc   2220
agtggttttg gtggcttccc tccacccttc ctgctggatt cttgcccaag cccagcccac   2280
atccggctca ctggggcgcc tctagccacg tgtgatgaga cctccatcta a             2331
```

<210> SEQ ID NO 3
<211> LENGTH: 776
<212> TYPE: PRT
<213> ORGANISM: Rattus norvegicus

<400> SEQUENCE: 3

```
Met Leu Ala Arg Ala Glu Arg Pro Arg Pro Gly Pro Arg Pro Pro Pro
  1               5                  10                  15

Val Phe Pro Phe Pro Pro Pro Leu Ser Leu Leu Leu Leu Leu Ala Ile
             20                  25                  30

Leu Ser Ala Pro Val Cys Gly Arg Val Pro Arg Ser Val Pro Arg Thr
         35                  40                  45

Ser Leu Pro Ile Ser Glu Ala Asp Ser Tyr Leu Thr Arg Phe Ala Ala
     50                  55                  60

Ser His Thr Tyr Asn Tyr Ser Ala Leu Leu Val Asp Pro Ala Ser His
 65                  70                  75                  80
```

-continued

```
Thr Leu Tyr Val Gly Ala Arg Asp Ser Ile Phe Ala Leu Thr Leu Pro
                85                  90                  95

Phe Ser Gly Glu Arg Pro Arg Arg Ile Asp Trp Met Val Pro Glu Thr
            100                 105                 110

His Arg Gln Asn Cys Arg Lys Lys Gly Lys Lys Glu Asp Glu Cys His
        115                 120                 125

Asn Phe Ile Gln Ile Leu Ala Ile Val Asn Ala Ser His Leu Leu Thr
    130                 135                 140

Cys Gly Thr Phe Ala Phe Asp Pro Lys Cys Gly Val Ile Asp Val Ser
145                 150                 155                 160

Ser Phe Gln Gln Val Glu Arg Leu Glu Ser Gly Arg Gly Lys Cys Pro
                165                 170                 175

Phe Glu Pro Ala Gln Arg Ser Ala Ala Val Met Ala Gly Gly Val Leu
            180                 185                 190

Tyr Thr Ala Thr Val Lys Asn Phe Leu Gly Thr Glu Pro Ile Ile Ser
        195                 200                 205

Arg Ala Val Gly Arg Ala Glu Asp Trp Ile Arg Thr Glu Thr Leu Ser
    210                 215                 220

Ser Trp Leu Asn Ala Pro Ala Phe Val Ala Ala Met Val Leu Ser Pro
225                 230                 235                 240

Ala Glu Trp Gly Asp Glu Asp Gly Asp Asp Glu Ile Phe Phe Phe Phe
                245                 250                 255

Thr Glu Thr Ser Arg Val Leu Asp Ser Tyr Glu Arg Ile Lys Val Pro
            260                 265                 270

Arg Val Ala Arg Val Cys Ala Gly Asp Leu Gly Gly Arg Lys Thr Leu
        275                 280                 285

Gln Gln Arg Trp Thr Thr Phe Leu Lys Ala Asp Leu Leu Cys Pro Gly
    290                 295                 300

Pro Glu His Gly Arg Ala Ser Gly Val Leu Gln Ala Met Ala Glu Leu
305                 310                 315                 320

Arg Pro Gln Pro Gly Ala Gly Thr Pro Ile Phe Tyr Gly Ile Phe Ser
                325                 330                 335

Ser Gln Trp Glu Gly Ala Ala Ile Ser Ala Val Cys Ala Phe Arg Pro
            340                 345                 350

Gln Asp Ile Arg Ala Val Leu Asn Gly Pro Phe Arg Glu Leu Lys His
        355                 360                 365

Asp Cys Asn Arg Gly Leu Pro Val Met Asp Asn Glu Val Pro Gln Pro
    370                 375                 380

Arg Pro Gly Glu Cys Ile Ala Asn Asn Met Lys Leu Gln Gln Phe Gly
385                 390                 395                 400

Ser Ser Leu Ser Leu Pro Asp Arg Val Leu Thr Phe Ile Arg Asp His
                405                 410                 415

Pro Leu Met Asp Arg Pro Val Phe Pro Ala Asp Gly Arg Pro Leu Leu
            420                 425                 430

Val Thr Thr Asp Thr Ala Tyr Leu Arg Val Val Ala His Arg Val Thr
        435                 440                 445

Ser Leu Ser Gly Lys Glu Tyr Asp Val Leu Tyr Leu Gly Thr Glu Asp
    450                 455                 460

Gly His Leu His Arg Ala Val Arg Ile Gly Ala Gln Leu Ser Val Leu
465                 470                 475                 480

Glu Asp Leu Ala Leu Phe Pro Glu Pro Gln Pro Val Glu Ser Met Lys
                485                 490                 495
```

-continued

```
Leu Tyr His Asp Trp Leu Leu Val Gly Ser His Thr Glu Val Thr Gln
            500                 505                 510

Val Asn Thr Ser Asn Cys Gly Arg Leu Gln Ser Cys Ser Glu Cys Ile
        515                 520                 525

Leu Ala Gln Asp Pro Val Cys Ala Trp Ser Phe Arg Leu Asp Ala Cys
    530                 535                 540

Val Ala His Ala Gly Glu His Arg Gly Met Val Gln Asp Ile Glu Ser
545                 550                 555                 560

Ala Asp Val Ser Ser Leu Cys Pro Lys Glu Pro Gly Glu His Pro Val
                565                 570                 575

Val Phe Glu Val Pro Val Ala Thr Val Gly His Val Val Leu Pro Cys
            580                 585                 590

Ser Pro Ser Ser Ala Trp Ala Ser Cys Val Trp His Gln Pro Ser Gly
        595                 600                 605

Val Thr Ala Leu Thr Pro Arg Arg Asp Gly Leu Glu Val Val Val Thr
    610                 615                 620

Pro Gly Ala Met Gly Ala Tyr Ala Cys Glu Cys Gln Glu Gly Gly Ala
625                 630                 635                 640

Ala Arg Val Val Ala Ala Tyr Ser Leu Val Trp Gly Ser Gln Arg Gly
                645                 650                 655

Pro Ser Asn Arg Ala His Thr Val Val Gly Ala Gly Leu Val Gly Phe
            660                 665                 670

Leu Leu Gly Val Leu Ala Ala Ser Leu Thr Leu Leu Leu Ile Gly Arg
        675                 680                 685

Arg Gln Gln Arg Arg Arg Gln Arg Glu Leu Leu Ala Arg Asp Lys Val
    690                 695                 700

Gly Leu Asp Leu Gly Ala Pro Pro Ser Gly Thr Thr Ser Tyr Ser Gln
705                 710                 715                 720

Asp Pro Pro Ser Pro Ser Pro Glu Asp Glu Arg Leu Pro Leu Ala Leu
                725                 730                 735

Gly Lys Arg Gly Ser Gly Phe Gly Gly Phe Pro Pro Pro Phe Leu Leu
            740                 745                 750

Asp Ser Cys Pro Ser Pro Ala His Ile Arg Leu Thr Gly Ala Pro Leu
        755                 760                 765

Ala Thr Cys Asp Glu Thr Ser Ile
    770                 775
```

<210> SEQ ID NO 4
<211> LENGTH: 2315
<212> TYPE: DNA
<213> ORGANISM: Homo sapiens
<220> FEATURE:
<221> NAME/KEY: misc_feature
<222> LOCATION: (1)..(1764)
<223> OTHER INFORMATION: Coding region
<220> FEATURE:
<221> NAME/KEY: 3'UTR
<222> LOCATION: (1765)..(2315)
<220> FEATURE:
<221> NAME/KEY: misc_feature
<222> LOCATION: (1)..(2315)
<223> OTHER INFORMATION: strandedness: double

<400> SEQUENCE: 4

```
gggggtgtcc tctatgctgc cactgtgaaa aactacctgg ggacggagcc aattatcacc      60

agagcagtgg gtcgtgccga ggactggatt cggacagata ccttgccttc ctggctgaac     120

gccccagcct ttgtcgcagc cgtggccttg agcccagccg aatgggggga tgaagatgga     180
```

-continued

```
gacgacgaaa tctacttctt ctttacggag acttcccgag catttgactc atacgagcgc    240

attaaagtcc cacgggtggc ccgtgtgtgt gcgggggacc tcgggggccg gaagaccctc    300

cagcagagat ggacgacgtt tttgaaagct gacctgctct gtccagggcc tgagcatggc    360

cgggcctcca gtgtcctgca ggatgttgct gtgcttcgac ctgagcttgg ggcagggact    420

cccatctttt atggcatctt ttcttcccag tgggaggggg ctactatctc tgctgtctgt    480

gccttccgac cacaagacat tcggacagtg ctgaatggtc ccttcagaga actaaaacat    540

gactgcaaca gaggactgcc tgtcgtggac aatgatgtgc cccagcccag acctggagag    600

tgcatcacca acaacatgaa gctccggcac tttggctcat ctctctccct gcctgaccgc    660

gtactcacct tcatccggga ccacccactc atggacaggc cagtgtttcc agctgatggc    720

cacccccctgc tggtcactac agatacagcc tatctcagag tcgtggccca cagggtgacc   780

agcctctcag ggaaagagta tgatgtgctc tacctgggga cagaggatgg acacctccac    840

cgagcagtgc ggatcggagc tcagctcagc gttcttgaag atctggcctt attcccagag    900

ccacagccag ttgagaacat gaaattgtac cacagctggc tcctggttgg ctcccgtact    960

gaggtgacac aagtgaatac aaccaactgt ggccgtctcc agagctgctc agagtgcatc   1020

ctggcccagg acccagtctg tgcctggagc ttccggctgg atgagtgtgt ggcccatgcc   1080

ggggagcacc gagggttggt ccaagacata gagtcagcag atgtctcctc tttgtgtcct   1140

aaagagcctg gagaacgtcc agtagtgttt gaagttcccg tggctacagc tgcgcatgtg   1200

gtcttgccat gttctccaag ctcagcatgg gcatcctgtg tgtggcacca gcccagtgga   1260

gtgactgcac tcaccccccg gcgggatgga ctggaggtgg tggtgacccc aggggccatg   1320

ggcgcttatg cctgtgaatg tcaggagggt ggggcagccc atgtggtagc agcttacagc   1380

ttggtatggg gcagccagcg agatgctccg agccgggccc acacagtggg ggcgggactg   1440

gctggcttct tcttggggat tctcgcagca tccctgactc tcattctgat tggtcggcgt   1500

cagcagcgac ggcgacagag ggaacttctg gctagagaca aggtgggcct ggacctgggg   1560

gctccacctt ctgggaccac aagctacagc caagaccctc cctccccctc tcctgaagat   1620

gagcggttgc cgctggccct ggccaagagg ggcagtggct ttggtggatt ctcaccaccc   1680

ttcctgcttg atccttgccc aagcccagcc cacattcggc taactggggc tcctctagcc   1740

acatgtgatg aaacatccat ctagagctgg gcaaatgacc actagtgtat aagtgatcac   1800

tggaacggag tgaccactga gatgctgggg gtcactgggc ctggaagacc atcccagcct   1860

ctgagttctc tttgagtatg agtgattact tggattttag tatctgttct ctctgagcct   1920

ggatgggctt ggggccagac ctttgcctga ttcctgattc ccatgagaaa tcagaactgc   1980

tttctgcagc aaatcagggc ttccccctaa catctgaact cctgtaaacc ttcatccctg   2040

gccccctatc ttgggcccat tagttttggg gatggggcac agggcatagc tatgactttg   2100

ctttctggtt ggagcctggc cggaaggaag agccctggag gtggttgggg gcaaatgtgc   2160

cctgagtcct tggggtggtt ctgcttattc ttcaagttta tctgaatctg tggggagtgc   2220

atgatcccca tgttgcaata tggagtctct gccctgagat cttccccatc tcagttttcc   2280

ttccatgaaa gagtacgtgt aaatacatag tgttc                               2315
```

<210> SEQ ID NO 5
<211> LENGTH: 1761
<212> TYPE: DNA
<213> ORGANISM: Homo sapiens
<220> FEATURE:
<221> NAME/KEY: misc_feature -continued
<222> LOCATION: (1)..(1761)
<223> OTHER INFORMATION: Coding region
<220> FEATURE:
<221> NAME/KEY: misc_feature
<222> LOCATION: (1)..(1761)
<223> OTHER INFORMATION: strandedness: double

<400> SEQUENCE: 5

```
gggggtgtcc tctatgctgc cactgtgaaa aactacctgg ggacggagcc aattatcacc     60
agagcagtgg gtcgtgccga ggactggatt cggacagata ccttgccttc ctggctgaac    120
gccccagcct ttgtcgcagc cgtggccttg agcccagccg aatgggggga tgaagatgga    180
gacgacgaaa tctacttctt ctttacggag acttcccgag catttgactc atacgagcgc    240
attaaagtcc cacgggtggc ccgtgtgtgt gcgggggacc tcgggggccg gaagaccctc    300
cagcagagat ggacgacgtt tttgaaagct gacctgctct gtccagggcc tgagcatggc    360
cgggcctcca gtgtcctgca ggatgttgct gtgcttcgac ctgagcttgg ggcagggact    420
cccatctttt atggcatctt ttcttcccag tgggaggggg ctactatctc tgctgtctgt    480
gccttccgac cacaagacat tcggacagtg ctgaatggtc ccttcagaga actaaaacat    540
gactgcaaca gaggactgcc tgtcgtggac aatgatgtgc cccagcccag acctggagag    600
tgcatcacca acaacatgaa gctccggcac tttggctcat ctctctccct gcctgaccgc    660
gtactcacct tcatccggga ccacccactc atggacaggc cagtgtttcc agctgatggc    720
cacccccctgc tggtcactac agatacagcc tatctcagag tcgtggccca cagggtgacc    780
agcctctcag ggaaagagta tgatgtgctc tacctgggga cagaggatgg acacctccac    840
cgagcagtgc ggatcggagc tcagctcagc gttcttgaag atctggcctt attcccagag    900
ccacagccag ttgagaacat gaaattgtac cacagctggc tcctggttgg ctcccgtact    960
gaggtgacac aagtgaatac aaccaactgt ggccgtctcc agagctgctc agagtgcatc   1020
ctggcccagg acccagtctg tgcctggagc ttccggctgg atgagtgtgt ggcccatgcc   1080
ggggagcacc gagggttggt ccaagacata gagtcagcag atgtctcctc tttgtgtcct   1140
aaagagcctg gagaacgtcc agtagtgttt gaagttcccg tggctacagc tgcgcatgtg   1200
gtcttgccat gttctccaag ctcagcatgg gcatcctgtg tgtggcacca gcccagtgga   1260
gtgactgcac tcacccccccg gcgggatgga ctggaggtgg tggtgacccc aggggccatg   1320
ggcgcttatg cctgtgaatg tcaggagggt ggggcagccc atgtggtagc agcttacagc   1380
ttggtatggg gcagccagcg agatgctccg agccgggccc acacagtggg ggcgggactg   1440
gctggcttct tcttggggat tctcgcagca tccctgactc tcattctgat tggtcggcgt   1500
cagcagcgac ggcgacagag ggaacttctg gctagagaca aggtgggcct ggacctgggg   1560
gctccacctt ctgggaccac aagctacagc caagaccctc cctccccctc tcctgaagat   1620
gagcggttgc cgctggccct ggccaagagg ggcagtggct ttggtggatt ctcaccaccc   1680
ttcctgcttg atccttgccc aagcccagcc cacattcggc taactggggc tcctctagcc   1740
acatgtgatg aaacatccat c                                             1761
```

<210> SEQ ID NO 6
<211> LENGTH: 587
<212> TYPE: PRT
<213> ORGANISM: Homo sapiens

<400> SEQUENCE: 6

```
Gly Gly Val Leu Tyr Ala Ala Thr Val Lys Asn Tyr Leu Gly Thr Glu
  1               5                  10                  15
```

-continued

```
Pro Ile Ile Thr Arg Ala Val Gly Arg Ala Glu Asp Trp Ile Arg Thr
            20                  25                  30

Asp Thr Leu Pro Ser Trp Leu Asn Ala Pro Ala Phe Val Ala Ala Val
        35                  40                  45

Ala Leu Ser Pro Ala Glu Trp Gly Asp Glu Asp Gly Asp Asp Glu Ile
    50                  55                  60

Tyr Phe Phe Phe Thr Glu Thr Ser Arg Ala Phe Asp Ser Tyr Glu Arg
65                  70                  75                  80

Ile Lys Val Pro Arg Val Ala Arg Val Cys Ala Gly Asp Leu Gly Gly
                85                  90                  95

Arg Lys Thr Leu Gln Gln Arg Trp Thr Thr Phe Leu Lys Ala Asp Leu
            100                 105                 110

Leu Cys Pro Gly Pro Glu His Gly Arg Ala Ser Ser Val Leu Gln Asp
        115                 120                 125

Val Ala Val Leu Arg Pro Glu Leu Gly Ala Gly Thr Pro Ile Phe Tyr
    130                 135                 140

Gly Ile Phe Ser Ser Gln Trp Glu Gly Ala Thr Ile Ser Ala Val Cys
145                 150                 155                 160

Ala Phe Arg Pro Gln Asp Ile Arg Thr Val Leu Asn Gly Pro Phe Arg
                165                 170                 175

Glu Leu Lys His Asp Cys Asn Arg Gly Leu Pro Val Val Asp Asn Asp
            180                 185                 190

Val Pro Gln Pro Arg Pro Gly Glu Cys Ile Thr Asn Asn Met Lys Leu
        195                 200                 205

Arg His Phe Gly Ser Ser Leu Ser Leu Pro Asp Arg Val Leu Thr Phe
    210                 215                 220

Ile Arg Asp His Pro Leu Met Asp Arg Pro Val Phe Pro Ala Asp Gly
225                 230                 235                 240

His Pro Leu Leu Val Thr Thr Asp Thr Ala Tyr Leu Arg Val Val Ala
                245                 250                 255

His Arg Val Thr Ser Leu Ser Gly Lys Glu Tyr Asp Val Leu Tyr Leu
            260                 265                 270

Gly Thr Glu Asp Gly His Leu His Arg Ala Val Arg Ile Gly Ala Gln
        275                 280                 285

Leu Ser Val Leu Glu Asp Leu Ala Leu Phe Pro Glu Pro Gln Pro Val
    290                 295                 300

Glu Asn Met Lys Leu Tyr His Ser Trp Leu Leu Val Gly Ser Arg Thr
305                 310                 315                 320

Glu Val Thr Gln Val Asn Thr Thr Asn Cys Gly Arg Leu Gln Ser Cys
                325                 330                 335

Ser Glu Cys Ile Leu Ala Gln Asp Pro Val Cys Ala Trp Ser Phe Arg
            340                 345                 350

Leu Asp Glu Cys Val Ala His Ala Gly Glu His Arg Gly Leu Val Gln
        355                 360                 365

Asp Ile Glu Ser Ala Asp Val Ser Ser Leu Cys Pro Lys Glu Pro Gly
    370                 375                 380

Glu Arg Pro Val Val Phe Glu Val Pro Val Ala Thr Ala Ala His Val
385                 390                 395                 400

Val Leu Pro Cys Ser Pro Ser Ser Ala Trp Ala Ser Cys Val Trp His
                405                 410                 415

Gln Pro Ser Gly Val Thr Ala Leu Thr Pro Arg Arg Asp Gly Leu Glu
            420                 425                 430
```

-continued

```
Val Val Val Thr Pro Gly Ala Met Gly Ala Tyr Ala Cys Glu Cys Gln
        435                 440                 445

Glu Gly Gly Ala Ala His Val Val Ala Ala Tyr Ser Leu Val Trp Gly
    450                 455                 460

Ser Gln Arg Asp Ala Pro Ser Arg Ala His Thr Val Gly Ala Gly Leu
465                 470                 475                 480

Ala Gly Phe Phe Leu Gly Ile Leu Ala Ala Ser Leu Thr Leu Ile Leu
                485                 490                 495

Ile Gly Arg Arg Gln Gln Arg Arg Arg Gln Arg Glu Leu Leu Ala Arg
            500                 505                 510

Asp Lys Val Gly Leu Asp Leu Gly Ala Pro Pro Ser Gly Thr Thr Ser
        515                 520                 525

Tyr Ser Gln Asp Pro Pro Ser Pro Ser Pro Glu Asp Glu Arg Leu Pro
    530                 535                 540

Leu Ala Leu Ala Lys Arg Gly Ser Gly Phe Gly Gly Phe Ser Pro Pro
545                 550                 555                 560

Phe Leu Leu Asp Pro Cys Pro Ser Pro Ala His Ile Arg Leu Thr Gly
                565                 570                 575

Ala Pro Leu Ala Thr Cys Asp Glu Thr Ser Ile
            580                 585


<210> SEQ ID NO 7
<211> LENGTH: 196
<212> TYPE: DNA
<213> ORGANISM: Homo sapiens
<220> FEATURE:
<221> NAME/KEY: misc_feature
<222> LOCATION: (1)..(196)
<223> OTHER INFORMATION: Coding region
<220> FEATURE:
<221> NAME/KEY: misc_feature
<222> LOCATION: (1)..(196)
<223> OTHER INFORMATION: strandedness: double

<400> SEQUENCE: 7

aaattgtacc acagctggct cctggttggc tcccgtactg aggtgacaca agtgaataca      60

accaactgtg gccgtctcca gagctgctca gagtgcatcc tggcccagga cccagtctgt     120

gcctggagct tccggctgga tgagtgtgtg gcccatgccg ggagcaccg agggttggtc      180

caagacatag agtcag                                                     196


<210> SEQ ID NO 8
<211> LENGTH: 30
<212> TYPE: DNA
<213> ORGANISM: Artificial Sequence
<220> FEATURE:
<223> OTHER INFORMATION: PCR primer used to obtain the sequence encoding
      the intracellular domain of Semaphorin W

<400> SEQUENCE: 8

gataaggatc cgggtcgccg tcagcagcgt                                       30


<210> SEQ ID NO 9
<211> LENGTH: 27
<212> TYPE: DNA
<213> ORGANISM: Artificial Sequence
<220> FEATURE:
<223> OTHER INFORMATION: Anti-sense PCR primer sequence used to obtain
      the sequence encoding the intracellular domain of Semaphorin W

<400> SEQUENCE: 9

ggctggaatt cattttcccc ggcttta                                          27
```

<210> SEQ ID NO 10
<211> LENGTH: 333
<212> TYPE: DNA
<213> ORGANISM: Homo sapiens
<220> FEATURE:
<221> NAME/KEY: misc_feature
<222> LOCATION: (1)..(333)
<223> OTHER INFORMATION: Coding region
<220> FEATURE:
<221> NAME/KEY: misc_feature
<222> LOCATION: (1)..(333)
<223> OTHER INFORMATION: strandedness: double

<400> SEQUENCE: 10

```
ccccggccgg gtcccgggca gcctacagcc tcgcccttcc cgctactgct gctggcggtg     60

ctgagcggcc cggtatccgg ccgcgtcccc cgctcggtgc ccagaacctc gcttccaatc    120

tctgaggctg acttctgtct cacccggttc gcagtccctc acacatacaa ttactctgtt    180

ctccttgtgg atcctgcctc ccacacactt tatgttggcg cccgggacac catcttcgct    240

ttatccctgc ccttctcagg ggagagaccc cgcaggattg actggatggt tcctgaggct    300

cacagacaga actgtaggaa gaaaggcaag aaa                                 333
```

<210> SEQ ID NO 11
<211> LENGTH: 111
<212> TYPE: PRT
<213> ORGANISM: Homo sapiens

<400> SEQUENCE: 11

```
Pro Arg Pro Gly Pro Gly Gln Pro Thr Ala Ser Pro Phe Pro Leu Leu
  1               5                  10                  15

Leu Leu Ala Val Leu Ser Gly Pro Val Ser Gly Arg Val Pro Arg Ser
             20                  25                  30

Val Pro Arg Thr Ser Leu Pro Ile Ser Glu Ala Asp Phe Cys Leu Thr
         35                  40                  45

Arg Phe Ala Val Pro His Thr Tyr Asn Tyr Ser Val Leu Leu Val Asp
     50                  55                  60

Pro Ala Ser His Thr Leu Tyr Val Gly Ala Arg Asp Thr Ile Phe Ala
 65                  70                  75                  80

Leu Ser Leu Pro Phe Ser Gly Glu Arg Pro Arg Arg Ile Asp Trp Met
                 85                  90                  95

Val Pro Glu Ala His Arg Gln Asn Cys Arg Lys Lys Gly Lys Lys
            100                 105                 110
```

<210> SEQ ID NO 12
<211> LENGTH: 7
<212> TYPE: PRT
<213> ORGANISM: Homo sapiens

<400> SEQUENCE: 12

```
Gln Asp Pro Val Cys Ala Trp
  1               5
```

<210> SEQ ID NO 13
<211> LENGTH: 7
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa = Gln or Arg
<220> FEATURE:

-continued

```
<221> NAME/KEY: misc_feature
<222> LOCATION: (6)..(6)
<223> OTHER INFORMATION: Xaa = Ala or Gly

<400> SEQUENCE: 13

Xaa Asp Pro Tyr Cys Xaa Trp
  1               5


<210> SEQ ID NO 14
<211> LENGTH: 14
<212> TYPE: PRT
<213> ORGANISM: Unknown
<220> FEATURE:
<223> OTHER INFORMATION: Description of Unknown Organism:  Myc tag

<400> SEQUENCE: 14

Asp Ile Gly Gly Glu Gln Lys Leu Ile Ser Glu Glu Asp Leu
  1               5                  10


<210> SEQ ID NO 15
<211> LENGTH: 364
<212> TYPE: DNA
<213> ORGANISM: Homo sapiens
<220> FEATURE:
<221> NAME/KEY: misc_feature
<222> LOCATION: (1)..(364)
<223> OTHER INFORMATION: sequence of GenBank Accession No: T09073
<220> FEATURE:
<221> NAME/KEY: misc_feature
<222> LOCATION: (1)..(364)
<223> OTHER INFORMATION: any n is a, g, c, t, unknown, or other

<400> SEQUENCE: 15

aaattgtacc acagctggct cctggttggc tcccgtactg aggtgacaca agtgaataca     60

acnaactgtg gccgtctcca gagctgctca gagtgcatcc tggcccagga cccagtctgt    120

gcctggagct tccggctgga tgagtgtgtg gcccatgccg gggagcaccg agggttggtc    180

caagacatag agtcagcaga tgtctcctct ttgtgtccta aagagcctgg agaacgtcca    240

gtagtgtttg aagttcccgt ggctacagnt gcgcatgtgg tcttnccatg ttctccaagc    300

tcagcatggg catcctgtgt gtggcaccag cccagtggag ttacttcact taccccccgg    360

cggg                                                                  364
```